US009795327B2

(12) United States Patent
Shoshihara et al.

(10) Patent No.: US 9,795,327 B2
(45) Date of Patent: Oct. 24, 2017

(54) MEASURING APPARATUS AND MEASUREMENT METHOD

(75) Inventors: Tomohiro Shoshihara, Kyoto (JP); Yasunori Shiraki, Kyoto (JP); Koji Katsuki, Kyoto (JP)

(73) Assignee: Arkray, Inc., Kyoto (JP)

( * ) Notice: Subject to any disclaimer, the term of this patent is extended or adjusted under 35 U.S.C. 154(b) by 564 days.

(21) Appl. No.: 13/377,994

(22) PCT Filed: Sep. 13, 2010

(86) PCT No.: PCT/JP2010/065708
§ 371 (c)(1),
(2), (4) Date: Dec. 13, 2011

(87) PCT Pub. No.: WO2011/037030
PCT Pub. Date: Mar. 31, 2011

(65) Prior Publication Data
US 2012/0215083 A1    Aug. 23, 2012

(30) Foreign Application Priority Data

Sep. 24, 2009  (JP) ................................. 2009-218794

(51) Int. Cl.
*A61B 5/05*  (2006.01)
*A61B 5/145*  (2006.01)
(Continued)

(52) U.S. Cl.
CPC ........ *A61B 5/14532* (2013.01); *A61B 5/0015* (2013.01); *A61B 5/14865* (2013.01); *A61B 5/6805* (2013.01)

(58) Field of Classification Search
CPC .. A61B 5/1473; A61B 5/1486; A61B 5/14532
(Continued)

(56) References Cited

U.S. PATENT DOCUMENTS 2,402,306 A * 6/1946 Turkel .................... A61M 5/32
128/DIG. 26
5,016,636 A * 5/1991 Kulakowski ......... A61B 5/1135
600/390
(Continued)

FOREIGN PATENT DOCUMENTS

| EP | 2327984 A2 | 6/2011 |
|---|---|---|
| JP | 2000-083933 A | 3/2000 |

(Continued)

OTHER PUBLICATIONS

International Search Report; PCT/JP2010/065708; dated Dec. 14, 2010.
(Continued)

*Primary Examiner* — Tiffany Weston
(74) *Attorney, Agent, or Firm* — Studebaker & Brackett PC

(57) ABSTRACT

Disclosed is a measuring device for obtaining numerical information concerning a substance present in the interstitial subcutaneous fluid, the device being equipped with a sensor unit that outputs signals in accordance with the numerical information concerning the substance and an arithmetic unit (control unit) that receives the signals outputted from the sensor unit and arithmetically processes the signals. The sensor unit is equipped with a sensor, some of which is punctured into the skin. The arithmetic unit (control unit) has been disposed so as to be separate from the sensor unit.

6 Claims, 18 Drawing Sheets

(51) Int. Cl.
*A61B 5/1486* (2006.01)
*A61B 5/00* (2006.01)

(58) Field of Classification Search
USPC .............................. 600/309, 345–347, 365
See application file for complete search history.

(56) References Cited

U.S. PATENT DOCUMENTS

| | | | |
|---|---|---|---|
| 5,230,350 | A * | 7/1993 | Fentress .................... 128/846 |
| 5,569,186 | A | 10/1996 | Lord et al. |
| 5,954,643 | A | 9/1999 | VanAntwerp et al. |
| 6,175,752 | B1 | 1/2001 | Say et al. |
| 6,230,035 | B1 | 5/2001 | Aoyagi et al. |
| 6,293,925 | B1 | 9/2001 | Safabash et al. |
| 6,520,326 | B2 | 2/2003 | McIvor et al. |
| 6,560,471 | B1 * | 5/2003 | Heller et al. .................. 600/347 |
| 6,565,509 | B1 | 5/2003 | Say et al. |
| 6,607,509 | B2 | 8/2003 | Bobroff et al. |
| 6,990,366 | B2 | 1/2006 | Say et al. |
| 7,310,544 | B2 | 12/2007 | Brister et al. |
| 7,494,465 | B2 | 2/2009 | Brister et al. |
| 7,497,827 | B2 | 3/2009 | Brister et al. |
| 2002/0023852 | A1 * | 2/2002 | Mcivor et al. ................. 206/305 |
| 2003/0004403 | A1 * | 1/2003 | Drinan et al. ................ 600/301 |
| 2005/0228340 | A1 * | 10/2005 | Cleary et al. .................. 604/46 |
| 2006/0036145 | A1 * | 2/2006 | Brister et al. ................ 600/345 |
| 2006/0202859 | A1 | 9/2006 | Mastrototaro et al. |
| 2007/0173711 | A1 | 7/2007 | Shah et al. |
| 2008/0313896 | A1 | 12/2008 | Shah et al. |
| 2009/0076340 | A1 * | 3/2009 | Libbus et al. ................ 600/301 |
| 2009/0076360 | A1 | 3/2009 | Brister et al. |
| 2010/0191084 | A1 | 7/2010 | Shah et al. |
| 2010/0324403 | A1 | 12/2010 | Brister et al. |
| 2011/0091816 | A1 | 4/2011 | Shah et al. |
| 2011/0091817 | A1 | 4/2011 | Shah et al. |
| 2011/0097480 | A1 | 4/2011 | Shah et al. |

FOREIGN PATENT DOCUMENTS

| | | |
|---|---|---|
| JP | 2005-128025 A | 5/2005 |
| JP | 2008-506468 A | 3/2008 |
| WO | 2006/017358 A1 | 2/2006 |
| WO | 2007/037970 A1 | 4/2007 |
| WO | 2009/035773 A1 | 3/2009 |

OTHER PUBLICATIONS

The Official Action issued by the Patent Office of the Russian Federation dated May 8, 2013, which corresponds to Russian Application No. 2012116245 and is related to U.S. Appl. No. 13/377,994 with translation.

The extended European search report dated Mar. 13, 2014, which corresponds to European Patent Application No. 10818705.5-1506 and is related to U.S. Appl. No. 13/377,994.

An Office Action issued by the Mexican Patent Office dated Dec. 10, 2013, which corresponds to Mexican Patent Application No. MX/a/2012/003571 and is related to U.S. Appl. No. 13/377,994.

* cited by examiner

MEASURING APPARATUS AND MEASUREMENT METHOD

TECHNICAL FIELD

The present invention relates to a measuring apparatus and a measurement method for measuring numeric information regarding substances contained in interstitial fluid and, in particular, glucose concentration.

BACKGROUND ART

In the case of traditional blood glucose level measurement, in order to collect blood, the body of the user has to be pierced with an instrument called a lancet at each measurement, which is problematic because it puts a heavy burden on the user and makes it impossible to perform continuous measurement.

In recent years, in order to eliminate such problems, a method has been proposed, in which blood glucose levels are measured in a continuous manner using CGM (Continuous Glucose Monitoring). In CGM, a sensor is partly deployed under the skin of the user and is used to measure the concentration of glucose in subcutaneous interstitial fluid (for example, see Patent Documents 1-3). While interstitial fluid is different from blood, the concentration of glucose in interstitial fluid matches the concentration of glucose in blood. Accordingly, a blood glucose level can be obtained by measuring the concentration of glucose in subcutaneous interstitial fluid. In addition, when CGM is used, the concentration of glucose in subcutaneous blood can also be measured directly through the deployed sensor.

Patent Documents 1-3 have disclosed a measuring apparatus used to measure glucose based on CGM. In addition, Patent Documents 1-3 have disclosed a method for deploying a sensor under the skin, as well as a device used in implementing said method. Here, the measuring apparatus disclosed in Patent Documents 1-3 will be described with reference to FIG. 18. FIG. 18 shows an example of a traditional measuring apparatus. In FIG. 18, the skin 104 is shown in cross-section.

As shown in FIG. 18, the measuring apparatus 100 includes a measurement unit 101, which has a sensor 103, and a receiving unit 105. Among these, the measurement unit 101 is placed on the surface of the user's skin 104. However, before the body of the measurement unit 101 is installed, a portion of the sensor 103 is embedded under the skin with the help of a dedicated piercing tool.

Specifically, the base portion 101a of the measurement unit 101 is first affixed to the surface of the user's skin 104 using adhesive tape 102. Next, a piercing tool (not shown), which has a sensor 103 installed therein, is attached to the base portion 101a.

The piercing tool is configured to enable ejection of the sensor 103 along with a piercing needle (not shown) and the user or medical personnel ejects the sensor 103 by operating the piercing tool. The ejected sensor 103, along with the needle, pierces and becomes lodged in the user's skin 104. The needle is then retracted and only the sensor 103 remains deployed under the skin of the user. After that, the piercing tool is removed and the body portion 101b of the measurement unit 101 is attached on top of the base portion 101a. At such time, the body portion 101b and the sensor 103 are electrically connected.

In addition, while not shown in FIG. 18, glucose oxireductase is immobilized on the distal end portion of the sensor 103. The sensor 103 has a pair of electrodes extending from its proximal portion to the distal end, with one of these electrodes (working electrode) placed in contact with the glucose oxireductase on the distal end portion. Accordingly, when a voltage is applied between the two electrodes, electric current flows between the two electrodes in proportion to the concentration of the glucose contained in subcutaneous interstitial fluid, such that the concentration of glucose can be determined from the value of the current.

Furthermore, while not shown in FIG. 18, the proximal portion of the sensor 103 is connected to electrical circuitry contained inside the body portion 101b. When an electric current flows between the electrodes of the sensor 103, the electrical circuitry generates an analog signal identifying its value and, furthermore, converts this analog signal to a digital signal. The electrical circuitry then transmits the digital signal on a carrier wave to the receiving unit 105. In addition, the measurement unit 101 contains a power supply, power circuits, etc. The receiving unit 105 computes a specific glucose concentration based on the received digital signal and displays the computed value on its display.

Thus, the measuring apparatus 100 shown in FIG. 18 lightens the burden on the user because it does not require the body of the user to be pierced at each measurement. In addition, it enables continuous measurement because the concentration of glucose can be measured as long as the sensor 103 is deployed.

CITATION LIST

Patent Document

Patent Document 1: U.S. Pat. No. 7,310,544
Patent Document 2: U.S. Pat. No. 7,494,465
Patent Document 3: U.S. Pat. No. 7,497,827

DISCLOSURE OF THE INVENTION

Problem to be Solved by the Invention

However, in the measuring apparatus 100 shown in FIG. 18 above, the measurement unit 101, due to its structure, protrudes from the human body 104 and when the user changes clothes, it may be easily caught on the clothes or come into contact with external objects. For this reason, there is a considerable chance that the measurement unit 101 and, furthermore, the sensor 103 may be dislodged from the skin 104.

In addition, due to the fact that the construction of the measurement unit 101 is such that it protrudes from the human body 104 to a considerable extent, when the unit is attached to a high-motion location, such as in the vicinity of a joint, the connection between the measurement unit 101 and the skin 104 cannot follow to movements of the human body and gradually becomes unstable. For this reason, in such a case there also is a considerable chance that, contrary to the intent of the user, the measurement unit 101 and, furthermore, the sensor 103 may be dislodged from the skin 104.

In addition, if the sensor 103 is dislodged from the skin 104 contrary to the intent of the user, the sensor 103 has to be inserted into the skin 104 once again, which puts a considerable burden on the user.

In addition, from the standpoint of hygiene, once the sensor 103 is dislodged from the skin 104, the sensor 103 has to be replaced with a new sensor regardless of the wishes of the user. In addition, in the measuring apparatus 100, the sensor 103 has to be connected to the electrical circuitry inside the measurement unit 101, which makes removal operations and attachment operations cumbersome and puts an even greater burden on the user. In addition, the user has to purchase a new sensor 103 and sensor replacement puts a considerable burden on the user in financial terms.

An example of the object of the present invention is to provide a measuring apparatus and a measurement method capable of eliminating the above-described problems and minimizing the occurrence of situations in which the sensor is dislodged contrary to the intent of the user and, at the same time, capable of facilitating the operation of sensor replacement.

Means for Solving the Problem

In order to attain the above-described object, the measuring apparatus according to an aspect of the present invention is a measuring apparatus that measures numeric information about a substance contained in at least one carrier selected from subcutaneous interstitial fluid and blood, wherein said apparatus includes a sensor section that has a sensor outputting a signal in accordance with the numeric information and a computing section receiving the signal outputted by the sensor and performing computational processing based on the signal, the sensor being formed such that a portion thereof can be deployed under the skin, and the computing section being disposed so as to be isolated from the sensor section.

Thus, the sensor is disposed away from the computing section, which contains electrical circuits etc. In addition, unlike the computing section, the sensor is not bulky. Accordingly, if the inventive measuring apparatus, monitoring apparatus, and sensor assembly are used, the occurrence of situations, in which the sensor is dislodged contrary to the intent of the user (for example, an end user), is minimized. Furthermore, even if sensor replacement is required when the computing section is attached to the human body, the sensor can be replaced in a simple manner on its own while leaving the computing section as it is. The inventive measuring apparatus can make the operation of sensor replacement easier.

In addition, an embodiment can be used, in which the computing section in the above-described measuring apparatus of the present invention is electrically connected to the sensor section through a wire. In such a case, a connecting structure that permits selection between a connected state and a disconnected state is preferably provided in the wire. As a result, sensor replacement can be performed in a simpler manner.

In addition, an embodiment can be used, in which the computing section in the above-described measuring apparatus of the present invention communicates with the sensor section via wireless communication. In this embodiment as well, sensor replacement can be made simpler, too.

In addition, in a preferred embodiment, the above-described measuring apparatus of the present invention is formed such that the sensor section further includes a water impermeable film having an adhesive layer on one side; the sensor includes a deployed portion deployed under the skin and a base portion disposed on the surface of the skin; and, the water impermeable film is formed so as to prevent the ingress of moisture to the base portion when it covers the base portion with the adhesive layer facing the base portion. This embodiment makes it possible to prevent moisture-induced sensor malfunction and, furthermore, protect the sensor from the outside.

In addition, in the above-described embodiment, the sensor section preferably further includes an adhesive film used to affix said sensor section to the skin. As a result, when the water impermeable film is replaced, the sensor can be prevented from being dislodged from the skin, which can facilitate the replacement of the water impermeable film.

In addition, in the above described case, the apparatus is preferably formed such that the sensor section includes, as the above-mentioned adhesive film, two or more pieces of adhesive film having an adhesive layer on one side; the two or more pieces of adhesive film being strip-like in shape and are capable of adhesion to both said sensor section and the skin through the medium of the adhesive layer in respectively different locations on the upper face of the sensor section. In such a case, the occurrence of situations, in which the base portion becomes dislodged from the skin when the water impermeable film is replaced can be further minimized.

An embodiment may be used, in which the above-described measuring apparatus of the present invention further includes a transmitting section that wirelessly transmits the outcome of the computational processing performed by the computing section to an external location; a housing that contains the computing section along with the transmitting section; and a receiver that receives the outcome of the computational processing transmitted by the transmitting section and displays numeric information about the substance based on the outcome of the computational processing.

In addition, in a preferred embodiment, the above-described measuring apparatus of the present invention further includes an amplifier circuit that amplifies the signal outputted by the sensor, and the amplifier circuit is provided in at least one location selected from the sensor section and the wire. According to this embodiment, the effects of the noise that affect the signal from the sensor can be reduced.

Furthermore, in the embodiment in which the computing section communicates with the sensor section via wireless communication, the above-described measurement apparatus of the present invention preferably further includes an amplifier circuit that amplifies the signal outputted by the sensor and the amplifier circuit is provided in at least one location selected from the sensor section and portions electrically connected to the sensor section. In such a case, the effects of the noise that affect the signal from the sensor can also be reduced.

In addition, in the above-described measuring apparatus of the present invention, the computing section is preferably disposed on the garment of the user utilizing said measuring apparatus. An improvement in user convenience is achieved in this case.

In addition, in order to attain the above-described object, the measurement method used in an aspect of the present invention is a measurement method for measuring numeric information about a substance contained in at least one carrier selected from subcutaneous interstitial fluid and blood, wherein said method includes the steps of: (a) disposing a sensor unit having a sensor outputting a signal in accordance with the numeric information on the skin such that a portion of the sensor is deployed under the skin, and (b) disposing a control unit that includes a computing section that receives the signal outputted by the sensor and performs computational processing based on the signal, in a location removed from the sensor unit.

In a preferred embodiment, the above-described measurement method of the present invention further includes the step of (c) electrically connecting the control unit to the sensor unit through a wire. In addition, in another preferred embodiment, the above-described measurement method of the present invention further includes the step of (d) allowing the control unit and the sensor unit to communicate via wireless communication.

Effects of the Invention

As described above, the present invention can minimize the occurrence of situations in which the sensor becomes dislodged contrary to the intent of the user and, furthermore, can facilitate the operation of sensor replacement.

BEST MODE FOR CARRYING OUT THE INVENTION

Embodiment 1

Figure 1:
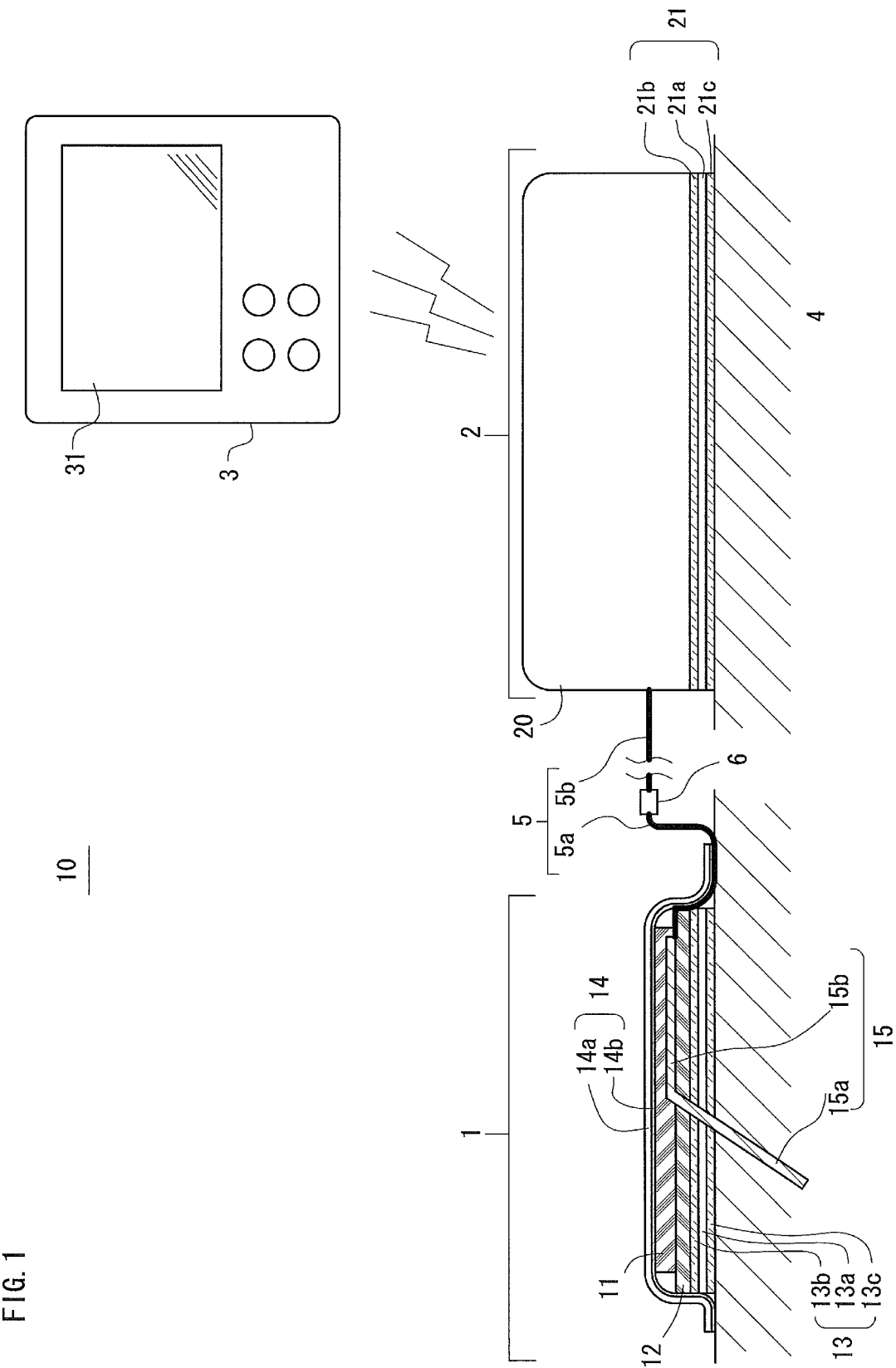
FIG. 1 is a block diagram illustrating the configuration of the measuring apparatus according to Embodiment 1 of the present invention, which is shown partially in cross-section.
Figure 2:
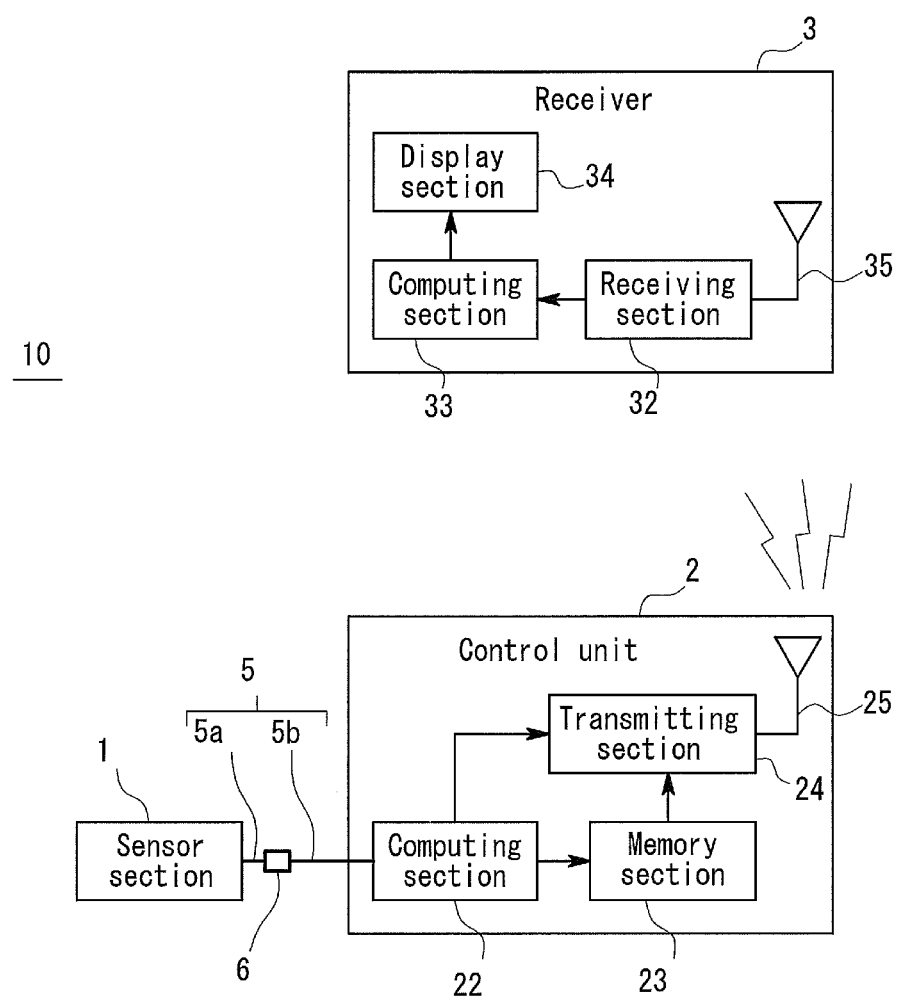
FIG. 2 is a block diagram illustrating the configuration of the measuring apparatus according to Embodiment 1 of the present invention.

The measuring apparatus, control unit, sensor, sensor unit, monitoring apparatus, sensor assembly, and measurement method according to Embodiment 1 of the present invention are described below with reference to FIGS. 1-4. First of all, the measuring apparatus, control unit, sensor, sensor unit, monitoring apparatus, and sensor assembly according to Embodiment 1 will be described with reference to FIGS. 1-4. FIG. 1 is a diagram illustrating the configuration of the measuring apparatus according to Embodiment 1 of the present invention. FIG. 2 is a block diagram illustrating the configuration of the measuring apparatus according to Embodiment 1 of the present invention. In FIG. 1, the measuring apparatus is shown partially in cross-section.

The measuring apparatus 10 according to Embodiment 1, which is shown in FIG. 1, is an apparatus that measures numeric information concerning at least one of a substance contained in subcutaneous interstitial fluid and a substance contained in subcutaneous blood. As shown in FIG. 1, the measuring apparatus 10 includes a sensor section 1. The sensor section 1 has a sensor 15 that outputs a signal in accordance with the numeric information.

The sensor 15 is formed such that a portion thereof can be deployed under the skin. In Embodiment 1, the sensor 15 includes a deployed portion 15a, which is deployed in the skin 4, and a base portion 15b, which is disposed on the surface of the skin 4.

In addition, as shown in FIG. 2, the measuring apparatus 10 includes a computing section 22 that receives the signal outputted by the sensor section 1 and performs computational processing based on the received signal. In Embodiment 1, the computing section 22 constitutes the control unit 2 shown in FIG. 1. In addition, the computing section 22 is implemented with electrical circuits and the electrical circuits are contained in the housing 20 (see FIG. 1) of the control unit 2. It should be noted that the specific configurations of the control unit 2 will be described below.

Furthermore, as shown in FIG. 1 and FIG. 2, the computing section 22 and control unit 2, in which it is provided, are disposed such that they are isolated from the sensor section 1. In addition, in Embodiment 1, the computing section 22 is electrically connected to the sensor section 1 through a wire 5.

Thus, in the measuring apparatus 10, the sensor 15 is disposed away from the control unit 2, which contains the computing section 22 (see FIG. 2). In addition, unlike the computing section 22 (control unit 2), the sensor 15 is not bulky. Therefore, the measuring apparatus 10 minimizes the occurrence of situations, in which the sensor 15 is dislodged contrary to the intent of the user (for example, an end user).

In addition, the control unit 2, which contains the computing section 22, can be attached to the skin 4 as described below. However, in such a case, even if the sensor 15 has to be replaced, the sensor 15 can be replaced on its own in a simple manner while leaving the control unit 2 as it is. For this reason, the measuring apparatus 10 can make facilitate the operation of replacement of the sensor 15.

Figure 3:
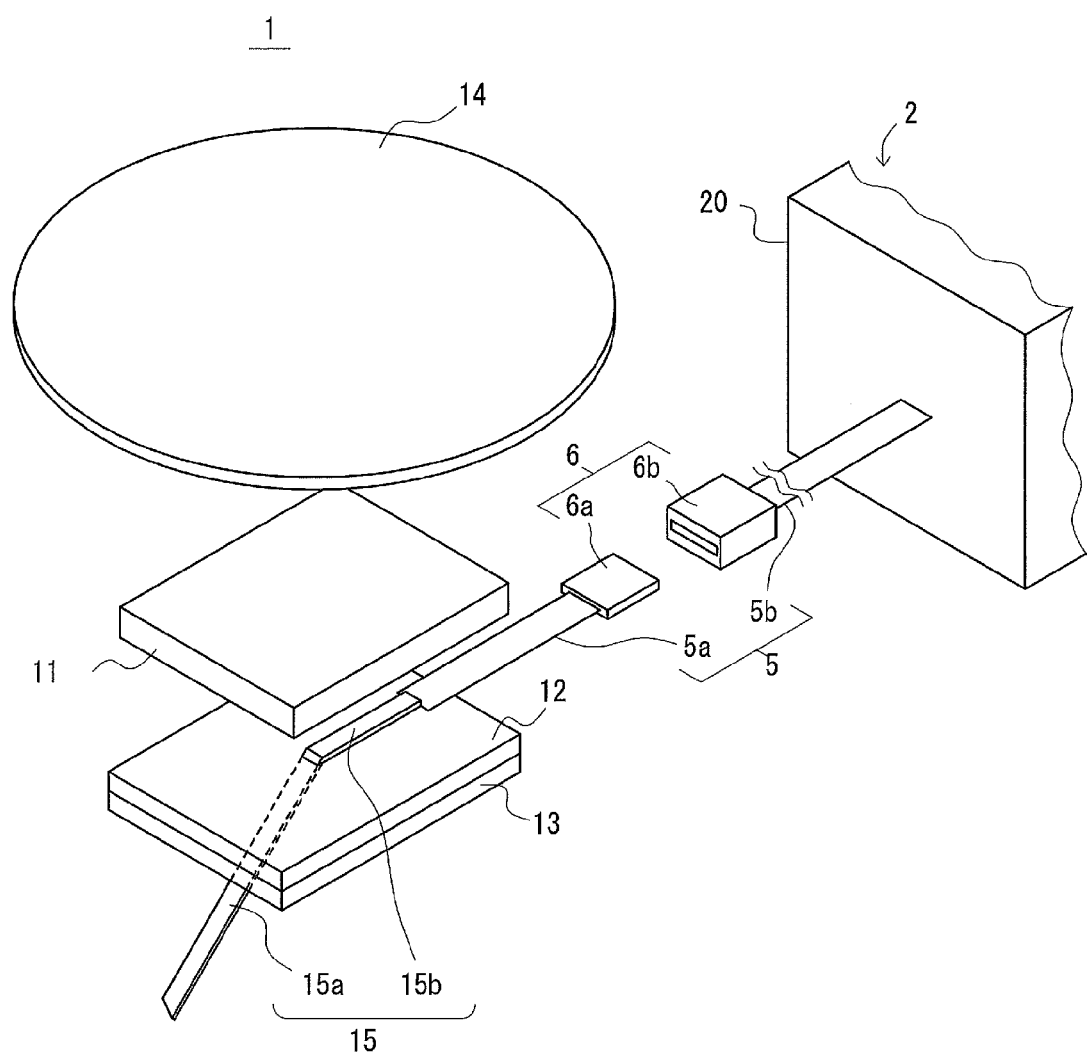
FIG. 3 is an exploded perspective view illustrating the configuration of the sensor section of the measuring apparatus shown in FIG. 1.
Figure 4:
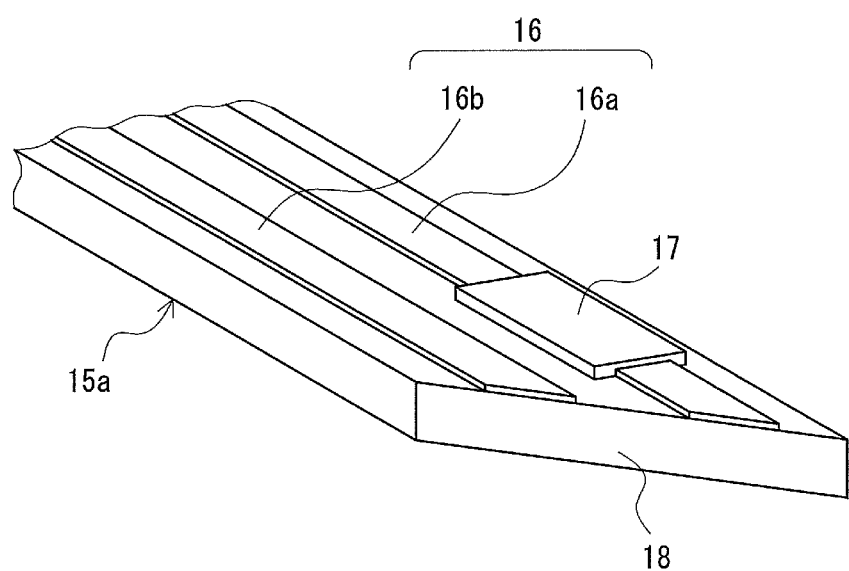
FIG. 4 is a perspective view illustrating the distal end portion of the sensor of the measuring apparatus shown in FIG. 1.

Here, the configuration of the measuring apparatus 10 will be described more specifically. First of all, the sensor section 1 will be specifically described with reference to FIG. 1 and FIG. 2, and, in addition, FIG. 3 and FIG. 4. FIG. 3 is an exploded perspective view illustrating the configuration of the sensor section of the measuring apparatus shown in FIG. 1. FIG. 4 is a perspective view illustrating the distal end portion of the sensor of the measuring apparatus shown in FIG. 1.

In Embodiment 1, the sensor section 1, which contains the sensor 15, constitutes a so-called sensor unit and is formed using a minimal configuration sufficient for attaching the sensor 15. Furthermore, this sensor unit is unable to independently operate the sensor 15 and can only operate the sensor 15 when connected to the control unit 2. In other words, the sensor section 1 (sensor unit) and control unit 2 are combined to form a sensor assembly. In addition, in Embodiment 1, glucose etc. contained in interstitial fluid or blood is suggested as the analyte substance and, furthermore, concentration etc. is suggested as the numeric information about the substance.

In addition, in Embodiment 1, the sensor 15 can output a signal corresponding to numeric information about the substance in a continuous manner. In such a case, the measuring apparatus 10 operates as a monitoring apparatus allowing for numeric information to be monitored on a continuous basis. In addition, when the measuring apparatus 10 operates as a monitoring apparatus, the measuring apparatus 10 can perform the above-described CGM if the numeric information about the substance is the concentration of glucose. It should be noted that the discussion below describes examples, in which the numeric information about the substance is the concentration of glucose and the sensor 15 is a glucose sensor.

As shown in FIG. 3, the deployed portion 15a and base portion 15b, which constitute the sensor 15, are both formed in an elongated band-like shape. In addition, the sensor 15 is disposed such that the deployed portion 15a is deployed under the skin (see FIG. 1) with the help of the piercing tools shown in Patent Documents 1-3 or other existing piercing tools. It should be noted that the deployed portion 15a is tilted relative to the base portion 15b. This is due to the fact that the piercing of the skin 4 with the deployed portion 15a using the piercing tools is carried out in a direction inclined relative to the normal of the skin 4 in order to make it easier for the deployed portion 15a to penetrate the skin 4.

In addition, although in the example of FIG. 3, the deployed portion 15a and base portion 15b are integrally formed using a substrate 18 (see FIG. 4), which possesses insulating properties and flexibility, Embodiment 1 is not limited to this form. For example, an embodiment may be used, in which the deployed portion 15a and the base portion 15b are formed separately from each other and connected after the deployed portion 15a is deployed. Furthermore, there are no particular limitations on the material of the substrate 18. However, thermoplastic resins, such as polyethylene terephthalate (PET), polypropylene (PP), polyethylene (PE), etc., and thermosetting resins, such as polyimide resins and epoxy resin, are suggested as the material of the substrate 18 from the standpoint of reducing its effects on the human body.

Furthermore, as shown in FIG. 4, in order to easily penetrate the skin 4, the distal end of the deployed portion 15a of the sensor 15 has a sharp shape. However, no particular limitations are imposed on the shape of the distal end and it may be formed in shapes other than the sharp shape. In addition, since the numeric information about the substance is the concentration of glucose, in Embodiment 1, the sensor 15, in addition to the substrate 18, includes a pair of electrodes 16a and 16b and a portion (enzyme immobilization portion) 17, on which glucose oxireductase is immobilized.

The electrodes 16a and electrodes 16b are formed in the longitudinal direction on the surface of the substrate 18 and are used to apply a voltage to the enzyme immobilization portion 17. The electrodes 16a and 16b can be formed, for instance, by screen printing etc. from electrically conductive materials such as carbon ink and the like.

The enzyme immobilization portion 17 is formed, for instance, by immobilizing glucose oxireductase on the electrode 16a. When glucose oxireductase reacts with glucose (substrate) in interstitial fluid or blood, it is reduced and generates hydrogen peroxide in proportion to the amount of the glucose. Therefore, when a voltage is applied between the electrodes 16a and 16b, electron transfer takes place between the electrodes 16a and 16b in proportion to the amount of the hydrogen peroxide, in other words, in proportion to the amount of the glucose. Thus, the glucose concentration can be determined by measuring the electric current flowing through the electrodes 16a and 16b.

In Embodiment 1, glucose oxidase (GOD) and glucose dehydrogenase (GDH), etc. are suggested as the suitable glucose oxireductases that can be used. Furthermore, various publicly-known methods are suggested as methods for immobilizing glucose oxireductase. Methods based on MPC polymers or methods utilizing protein membranes can be suggested as examples. It should be noted that MPC polymers are polymers that can be obtained by introducing silane coupling agents into phospholipid polymers containing phosphorus, polyacrylamide, and polymeric gels.

As shown in FIG. 1 and FIG. 3, in Embodiment 1, the sensor section 1, in addition to the sensor 15, includes a support film 12 that supports the sensor 15, a protective film 11 that protects the top surface of the sensor 15, and a water impermeable film 14.

When the deployed portion 15a extends through the support film 12 and the base portion 15b is disposed on the support film 12, the sensor 15 is supported by the support film 12. It should be noted that the piercing of the support film 12 by the deployed portion 15a can be accomplished with the help of the above-mentioned piercing tools. In addition, a through-hole for inserting the deployed portion 15a into the support film 12 may be provided in advance. In this case, the operation of replacement of the sensor 15 can be facilitated.

In addition, as shown in FIG. 1 and FIG. 3, the protective film 11 is disposed on the support film 12 such that the base portion 15b is sandwiched therebetween. The base portion 15b is affixed to the protective film 11 and support film 12 with an adhesive agent (not shown in FIG. 1 and FIG. 3).

The water impermeable film 14 has an adhesive layer (not shown in FIG. 3) on one side. In addition, the water impermeable film 14 is formed such that when it covers the base portion 15b, with the adhesive layer facing the base portion 15b, the ingress of moisture to the base portion 15b is prevented.

Specifically, as shown in FIG. 1 and FIG. 3, the water impermeable film 14 is formed such that its surface area is larger in comparison with the surface area of the support film 12 and, place on top of the protective film 11, it covers the base portion 15b. Since the base portion 15b is connected to the wire 5, penetration of moisture into the connecting portion between the base portion 15b and the wire 5 results in malfunction of the sensor 15. However, in Embodiment 1, moisture-induced sensor malfunction can be prevented and, furthermore, the sensor 15 can be protected from the outside.

In addition, the water impermeable film 14 can be formed, for instance, by providing an adhesive material layer made of an acrylic-based adhesive material etc. on one side of a piece of filmic base material formed from polyurethane resin or polyester resin, etc.

In addition, as shown in FIG. 1 and FIG. 3, the sensor section 1 further includes an adhesive film 13 for affixing it to the skin 4. Specifically, the adhesive film 13 is provided on the bottom surface of the support film 12 and affixes the sensor section 1 to the skin 4. Furthermore, the deployed portion 15a of the sensor 15 also extends through the adhesive film 13. It should be noted that, in the same manner as the support film 12, the adhesive film 13 can be pierced by the deployed portion 15a with the help of the above-described piercing tools. In addition, in the same manner as in the case of the support film 12, a through-hole for inserting the deployed portion 15a into the adhesive film 13 may be provided in advance in the same manner as in the case of the support film 12.

In addition, as shown in FIG. 1, a double-sided tape can be used as the adhesive film 13. The adhesive film 13 includes a base material 13a, an adhesive layer 13b provided on one side of the substrate 13a, and an adhesive layer 13c provided on the other side.

Thus, in Embodiment 1, the sensor 15 is affixed to the skin 4 by the adhesive film 13. As a result, when the water impermeable film 14 is replaced, the dislodgement of the sensor 15 from the skin 4 can be minimized, which can make the replacement of the water impermeable film 14 easier.

In addition, because of the large surface area of direct contact between the skin 4 and the adhesive film 13, the latter should preferably cause little irritation to the skin 4. Specifically, the adhesive film 13 can be formed by providing an adhesive material layer made of a hydrogel-based adhesive material or a silicone-based adhesive material, etc. on both sides of a piece of base material formed from nonwoven fabric, etc. It should be noted that Embodiment 1 may be an embodiment, in which only the above-described adhesive material layer is provided instead of the adhesive film 13.

Furthermore, in Embodiment 1, as shown in FIGS. 1-3, the wire 5, which connects the sensor section 1 (sensor 15) to the computing section 22 (control unit 2), is electrically connected to the electrodes 16a and 16b shown in FIG. 4. In addition, a connecting structure (hereinafter referred to as the "connector") 6, which permits selection between a connected state and a disconnected state, is preferably provided in the wire 5.

Specifically, the wire 5 is composed of a wire 5a, which extends from the sensor 15 of the sensor section 1, and a wire 5b, which extends from the control unit 2. In other words, the sensor 15 includes a wire 5a for external connections, and the control unit 2 includes a wire 5b for external connections. Additionally, a male terminal 6a, which forms part of the connector 6, is provided at one end of the wire 5a and a female terminal 6b, which forms part of the connector 6, is provided at one end of the wire 5b.

Thus, if the connector 6 is provided in the wire 5, then, even if the sensor 15 has to be replaced when the control unit 2 is affixed to the skin 4, the sensor 15 (sensor section 1) can be replaced on its own in a simple manner, with the control unit 2 still attached. In addition, in the example shown in FIGS. 1-3, the connector 6 is provided on the side of the wire 5 that is closer to the sensor section 1. In other words, the length of the wire 5a is shorter than the length of the wire 5b. This is due to the fact that the wire 5a, which extends from the sensor section 1, is preferably as short as possible such that the wire 5a does not affect the operation of deployment of the sensor 15. It should be noted that, in contradistinction to the example shown in FIGS. 1-3, in the present embodiment, the connector 6 may be provided on the side that is closer to the control unit 2, and, in such a case, the female terminal 6b may be attached to the housing 20.

The configuration of the measuring apparatus 10 in terms of components other than the sensor section 1 will be hereinafter specifically described with reference to FIG. 1 and FIG. 2. As shown in FIG. 1 and FIG. 2, in Embodiment 1, the measuring apparatus 10 further includes a receiver 3. The receiver 3 is situated in a location physically removed from both the sensor section 1 and the control unit 2 and displays the concentration of the substance, i.e. glucose, in interstitial fluid on a display screen 31 (see FIG. 1) based on the outcome of the computational processing carried out by the computing section 22.

As shown in FIG. 2, in order to transmit the outcome of the computational processing performed by the computing section 22 to the receiver 3, the measuring apparatus 10 includes a transmitting section 24, which wirelessly transmits the outcome of the computational processing to an external location. The transmitting section 24, along with the computing section 22, is contained inside the housing 20 (see FIG. 2) of the control unit 2. Furthermore, in the same manner as the computing section 22, the transmitting section 24 can also be implemented with electrical circuits and the electrical circuits of both may be provided on the same substrate. In addition, the electrical circuits may be composed of IC chips.

In addition, as shown in FIG. 2, a memory section 23 is contained inside the housing 20 of the control unit 2. The memory section 23 stores information that identifies the outcome of the computational processing performed by the computing section 22.

In Embodiment 1, when an electric current flows between the electrodes 16a and 16b (see FIG. 4) of the sensor 15, the computing section 22 generates an analog signal identifying its value and, furthermore, converts this analog signal to a digital signal. In addition, along with storing information identified by the obtained digital signal in the memory section 23, the computing section 22 notifies the transmitting section 24 that computational processing has been performed.

When the transmitting section 24 receives the notification of completion of computational processing from the computing section 22, it retrieves the information stored in the memory section 23 and transmits it on a carrier wave. In FIG. 2, the numeral 25 designates a transmitting antenna.

In addition, while not shown in FIG. 2, the control unit 2 contains a power supply, power circuits, etc. Furthermore, as shown in FIG. 1, the control unit 2 is affixed to the skin 4 using a double-sided tape 21. The double-sided tape 21 includes a base material 21a, an adhesive layer 21b provided on one side of the base material 21a, and an adhesive layer 21c provided on the other side.

As shown in FIG. 2, the receiver 3 includes a receiving section 32, a computing section 33, a display section 34, and a receiving antenna 35. The receiving section 32 receives radio waves transmitted from the transmitting section 24, retrieves information therefrom, and supplies the retrieved information to the computing section 33. The supplied information identifies the current value detected by the sensor 15 and, based on the received information, the computing section 33 computes a specific glucose concentration and supplies the computed value to the display section 34. The display section 34 displays the computed value on the display screen 31 (see FIG. 1).

In addition, in Embodiment 1, in order to minimize the effects of the noise that affect the electric current (current signal) from the sensor 15, an amplifier circuit is preferably provided in at least one location selected from the sensor section 1, wire 5, and connector 6. In such a case, an improvement in the accuracy of glucose concentration measurement is achieved because the current signal is amplified and the effects of noise are minimized. In addition, the supply of electric power to the amplifier circuit can be accomplished by the control unit 2 through the wire 5. Furthermore, the IC chip constituting the amplifier circuit is minuscule (for example, 5 mm long by 5 mm wide by 1.5 mm thick). Therefore, it is believed that even in the embodiment in which an amplifier circuit is disposed in the sensor section 1, the sensor section 1 is not going to be bulky.

Thus, since in Embodiment 1 the sensor section 1 has a thin shape that is unlikely to come into contact with external objects, it is not likely to be affected by external forces and the occurrence of situations, in which the sensor 15 becomes dislodged under the action of external forces, is minimized. In addition, since the sensor section 1 can be disposed in a location removed from the control unit 2, even when the control unit 2 adhered to the skin 4 is dislodged under the action of external forces, the occurrence of situations, in which the sensor 15 is also dislodged as a result, is minimized. Furthermore, the sensor section 1 can be retrieved in a simple manner and easily replaced regardless of the state of the control unit 2 simply by removing the connector 6 from the control unit 2.

In addition, as shown in FIG. 1, the measurement method of Embodiment 1 can be implemented by disposing the sensor section 1 (sensor unit) and control unit 2 on the skin 4 and operating them. In other words, the measurement method is implemented by using the computing section 22 to perform computational processing on the signal from the sensor section 1 in a continuous manner or at regular intervals.

Specifically, the measurement method of Embodiment 1 includes the following steps (1)-(10) (see FIG. 1-FIG. 3).

(1) Disposing a sensor unit (sensor section 1), which includes a sensor 15, on the skin 4 such that a deployed portion 15a of the sensor is deployed under the skin.

(2) Electrically connecting a control unit 2, which includes a computing section 22, to the sensor unit through a wire 5.

(3) Disposing the control unit 2 in a location removed from the sensor unit.

(4) Affixing the sensor unit to the skin 4 using an adhesive film 13.

(5) Covering the base portion 15b with a water impermeable film 14 having an adhesive layer 14b on one side, with the adhesive layer 14b facing the base portion 15b of the sensor 15, and thereby preventing the penetration of moisture into the base portion 15b.

(6) Directing the sensor 15 to output the signal.

(7) If an amplifier circuit is provided, amplifying the signal outputted by the sensor 15.

(8) Directing the computing section 22 to perform computational processing.

(9) Wirelessly transmitting the outcome of the computational processing to an external location.

(10) Receiving the transmitted outcome of computational processing using a receiver 3 and displaying numeric information about the substance based on the outcome of the computational processing.

In addition, in the foregoing, the order of performance of the steps is not limited to the numbers assigned to the steps. For example, the steps may be performed in the following order: (1) (4), (5), (3), (2), (6), (7), (8), (9), and (10).

Embodiment 2

Figure 5:
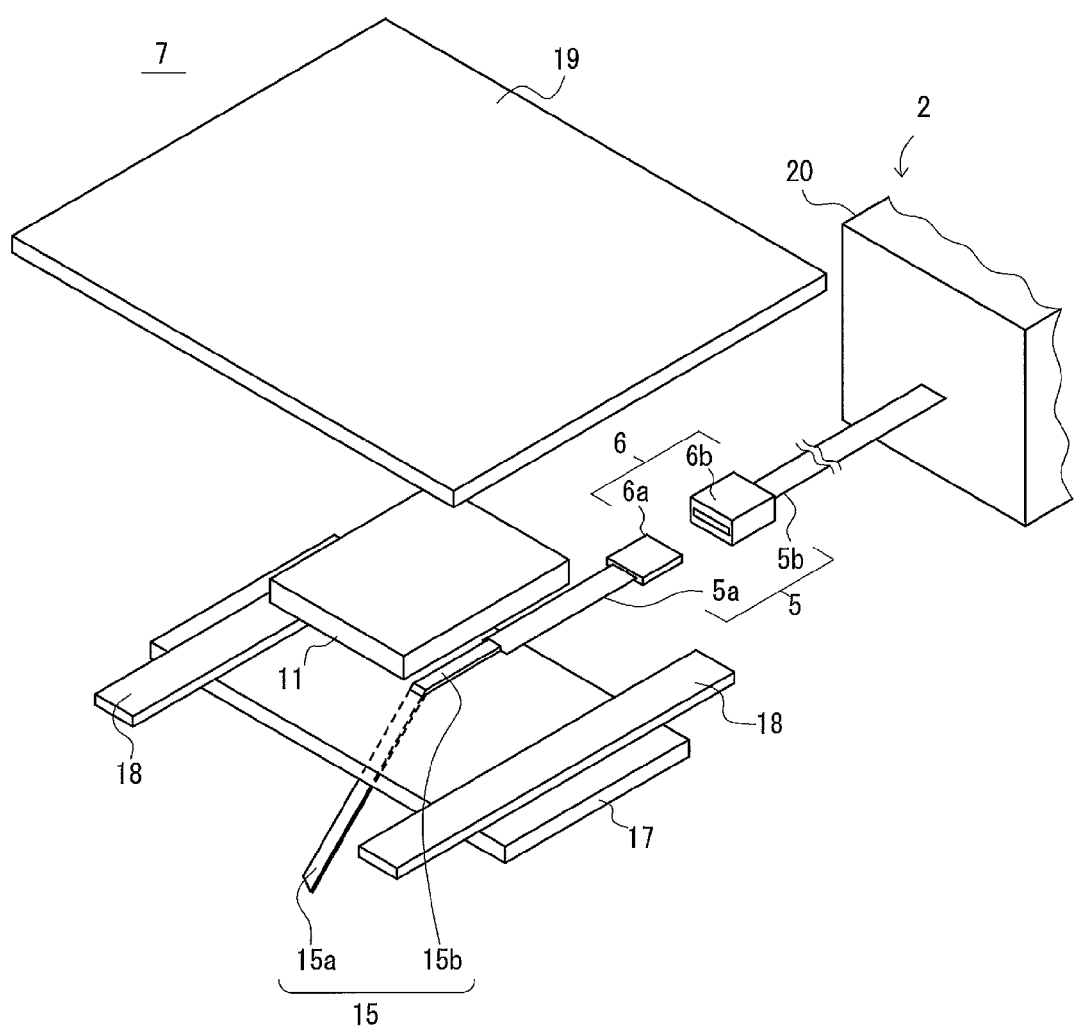
FIG. 5 is an exploded perspective view illustrating the configuration of the sensor section of the measuring apparatus according to Embodiment 2 of the present invention.

Next, the measuring apparatus according to Embodiment 2 of the present invention will be explained with reference to FIG. 5. FIG. 5 is an exploded perspective view illustrating the configuration of the sensor section of the measuring apparatus according to Embodiment 2 of the present invention.

In contradistinction to the measuring apparatus 10 according to Embodiment 1, the measuring apparatus according to Embodiment 2 includes a sensor section 7 instead of the sensor section 1 shown in FIGS. 1-3. However, in respects other than the sensor section 7, the measuring apparatus of Embodiment 2 is similar to the measuring apparatus 10 of Embodiment 1. In addition, in the description that follows, only those points that differ will be discussed.

As shown in FIG. 5, in the same manner as the sensor section 1 shown in FIG. 3, the sensor section 7 includes a sensor 15 and a protective film 11. However, the sensor section 7 differs from the sensor section 1 in the configuration of the adhesive film 18 and support film 17, on which the base portion 15b of the sensor 15 is disposed.

In Embodiment 2, the shape of the support film 17 is longer and narrower than the shape of the support film 12. This is in order to facilitate affixing to the skin using the adhesive film 18, which is described below.

Unlike the adhesive film 13 shown in FIG. 3, the adhesive film 18 has an adhesive layer (not shown in FIG. 2) only on one side. In addition, two pieces of film are used as the adhesive film 18. Furthermore, the two pieces of the adhesive film 18 are strip-like in shape and are formed such that they can be adhered to both the sensor section 7 and to the skin through the medium of the adhesive layers in respectively different locations on the upper face side of the sensor section 7.

Specifically, they are formed in such a manner that when each piece of the adhesive film 18 is adhered along the short edge direction of the support film 17 on the side of the support film 17 opposite the side facing the skin (referred to as the "upper face side"), both ends thereof are adhered to the skin and the central portions are adhered to the support film 17.

Thus, in Embodiment 2, the sensor section 7 is affixed to the skin using the two pieces of the adhesive film 18. For this reason, when the water impermeable film 19 is replaced, the chances that the sensor 15 will be dislodged from the skin 4 can be reduced in comparison with Embodiment 1. If Embodiment 2 is used, the replacement of the water impermeable film 19 can be made even easier.

Incidentally, since the adhesive film used to affix the sensor unit to the skin is in direct contact with the skin, periodic replacement of the adhesive film is required for hygienic purposes. In addition, since in accordance with Embodiment 1 the sensor unit (sensor section 1) has a structure in which its bottom side is affixed using the adhesive film 13 and, furthermore, the sensor 15 extends through the adhesive film 13, when the adhesive film 13 is replaced, the sensor 15 also needs to be replaced. In addition, since at such time the sensor 15 cannot be re-used even if the useful life of the sensor 15 has not been completely exhausted, the retrieved sensor 15 is discarded.

On the other hand, although periodic replacement of the adhesive film 18 is required in Embodiment 2 in the same manner, in Embodiment 2, due to its construction, the adhesive film 18 can be replaced on its own without retrieving the sensor 15 at such time. In accordance with Embodiment 2, there is no need to replace the sensor 15 in a mandatory manner because the adhesive film 18 can be replaced on its own, which makes it possible to avoid wasting sensors 15. In additions, since the adhesive film 18 can be replaced in a sequential manner, the occurrence of misregistration of the sensor 15 during replacement is minimized.

In addition, while the number of the adhesive film strips 18 in Embodiment 2 is two or more, it is not particularly limited. Furthermore, since the surface area of the support film 17 in Embodiment 2 is larger than the surface area of the support film 12 shown in FIG. 3, the surface area of the water impermeable film 19 is correspondingly larger than the surface area of the water impermeable film 14 shown in FIG. 3.

In addition, the measurement method according to Embodiment 2 includes the Steps (1)-(10) described in Embodiment 1. However, as shown in FIG. 5, in Step (4), Embodiment 2 uses two or more pieces of adhesive film 18 that have an adhesive layer on one side (not shown in FIG. 5) and are strip-like in shape. The adhesive film 18 is adhered to both the sensor unit and the skin with the help of the adhesive layers in respectively different locations on the upper face side of the sensor unit.

Embodiment 3

The measuring apparatus, control unit, sensor, sensor unit, monitoring apparatus, sensor assembly, and measurement method according to Embodiment 3 of the present invention will be hereinafter described with reference to FIG. 6-FIG. 9.

Figure 6:
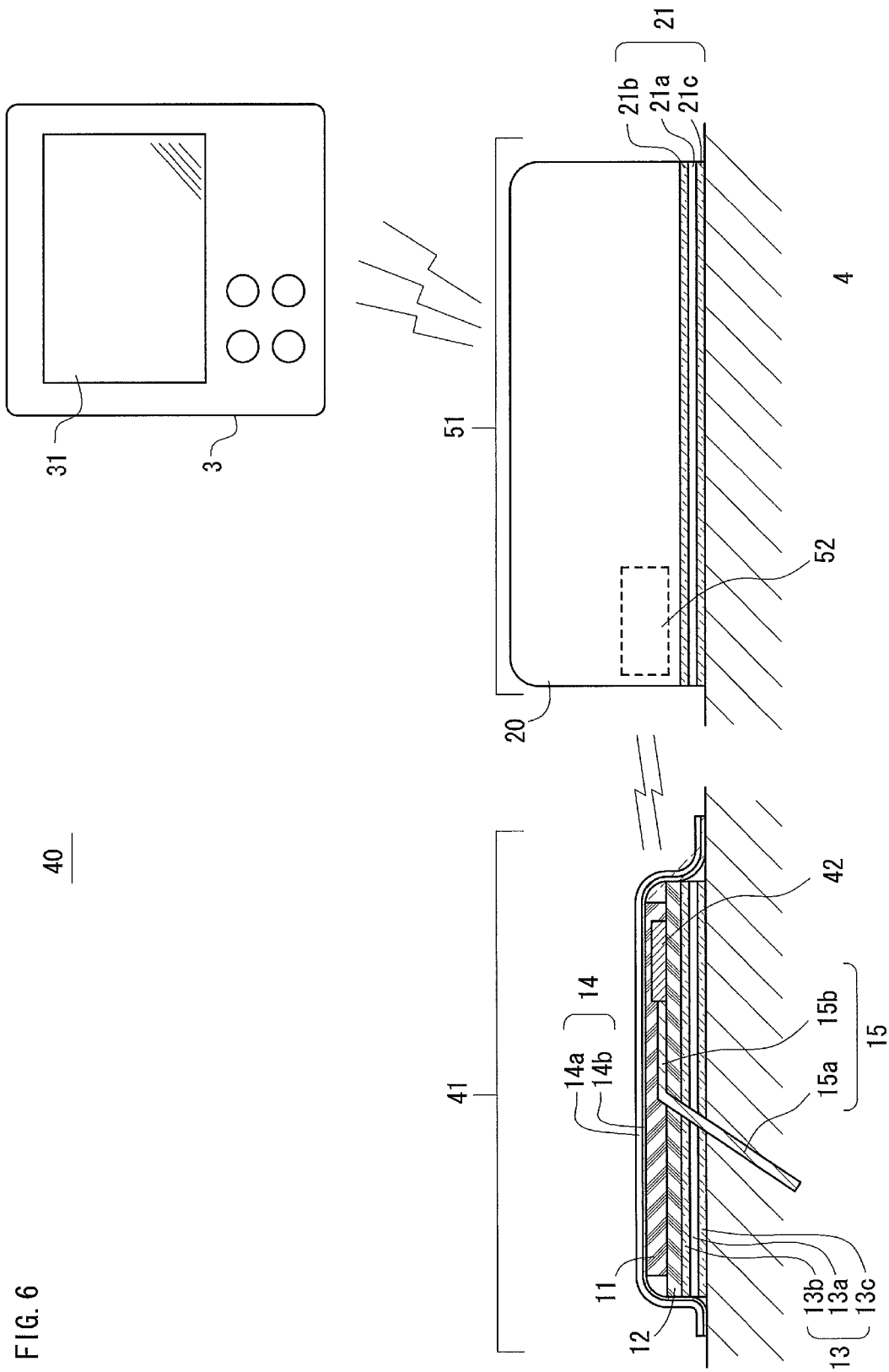
FIG. 6 is a block diagram illustrating the configuration of the measuring apparatus according to Embodiment 3 of the present invention, which is shown partially in cross-section.
Figure 7:
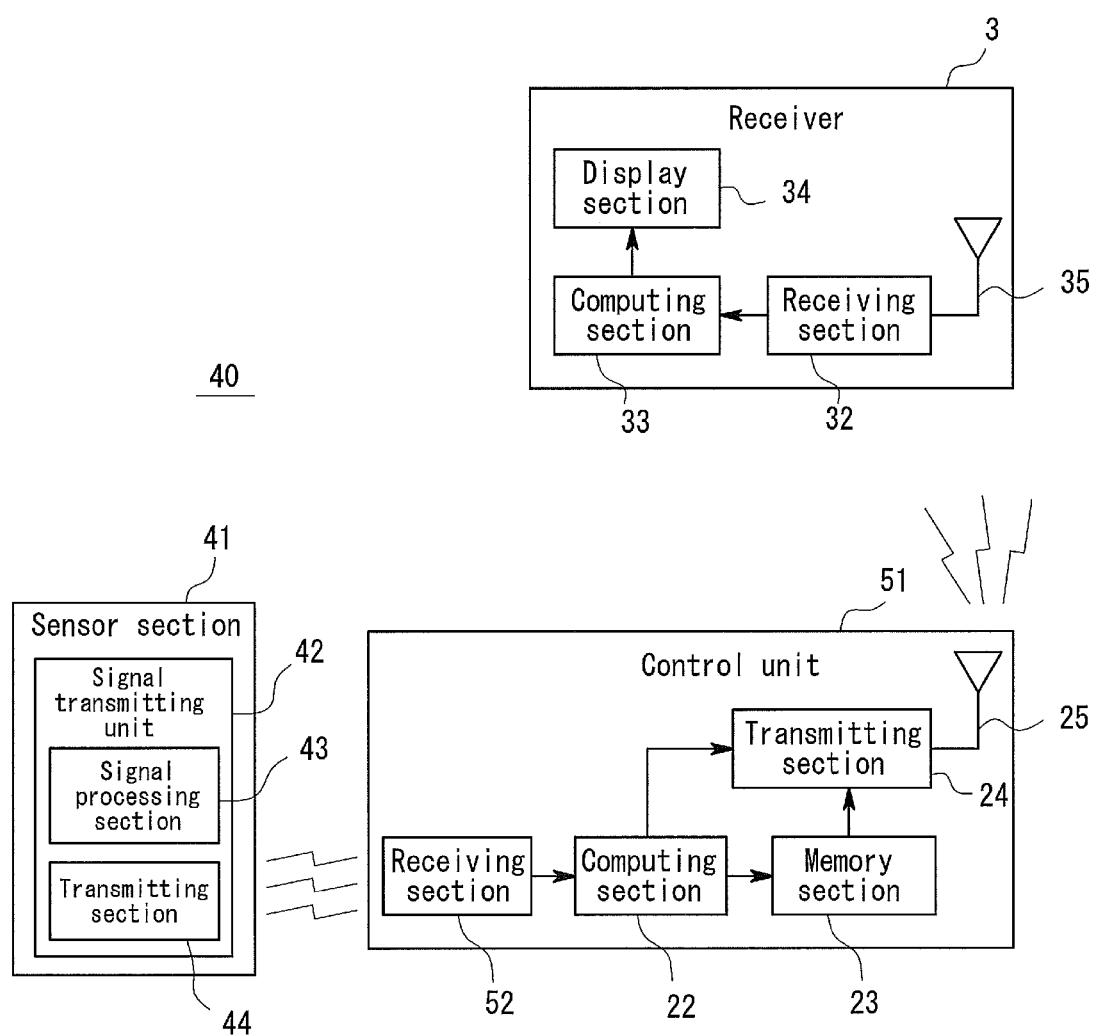
FIG. 7 is a block diagram illustrating the configuration of the measuring apparatus according to Embodiment 3 of the present invention.
Figure 8:
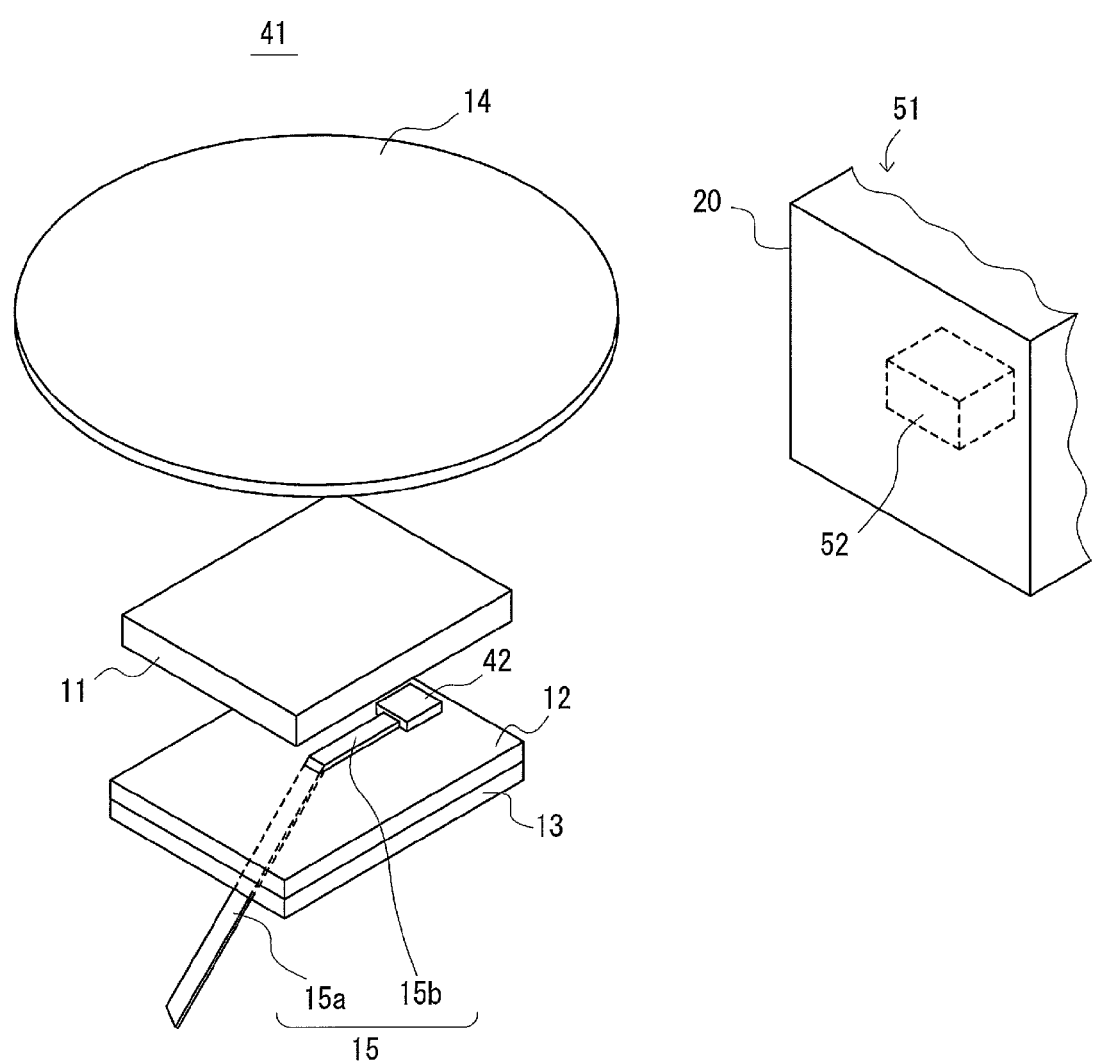
FIG. 8 is an exploded perspective view illustrating the configuration of the sensor section of the measuring apparatus shown in FIG. 6.
Figure 9:
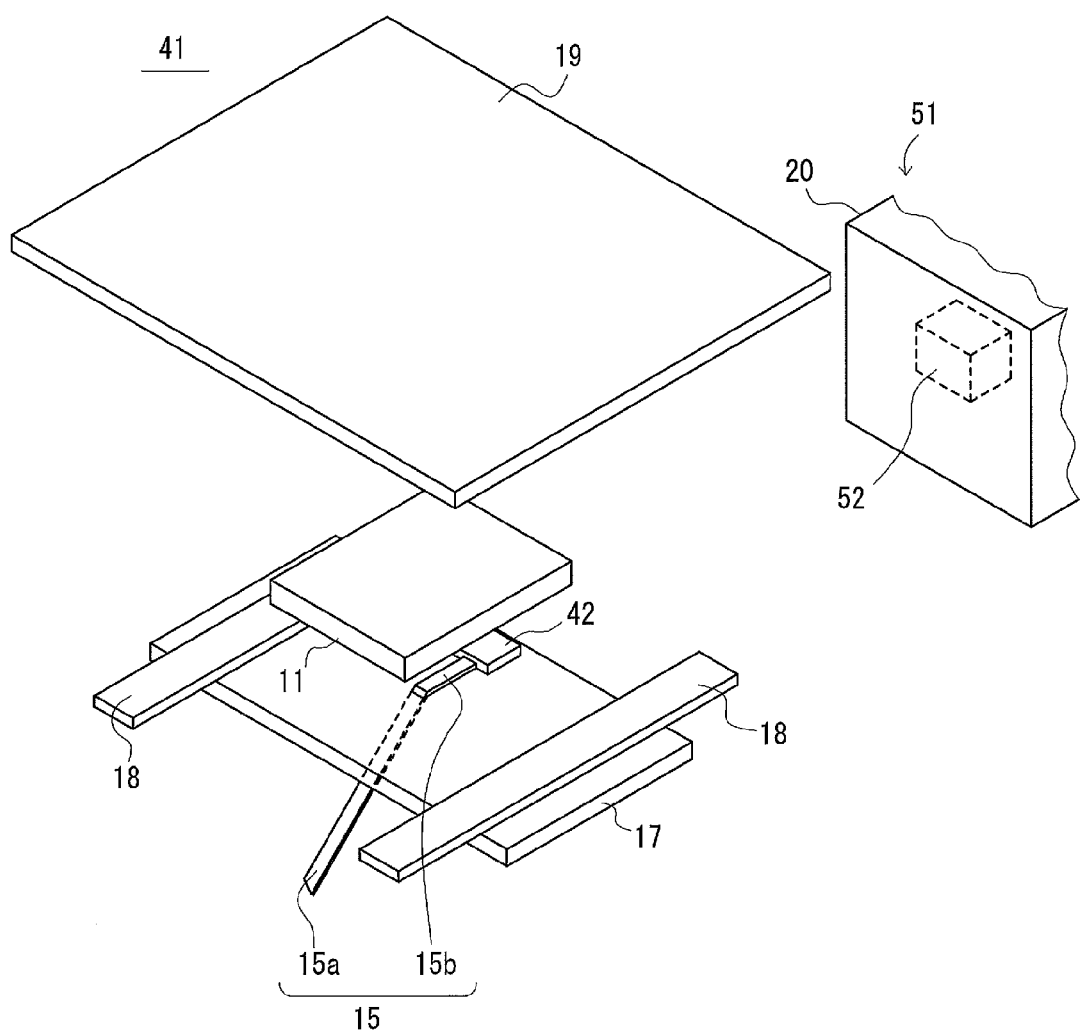
FIG. 9 is an exploded perspective view illustrating the configuration of another example of the sensor section according to Embodiment 3 of the present invention.

FIG. 6 is a diagram illustrating the configuration of the measuring apparatus according to Embodiment 3 of the present invention. In FIG. 6, the measuring apparatus is shown partially in cross-section. FIG. 7 is a block diagram illustrating the configuration of the measuring apparatus according to Embodiment 3 of the present invention. FIG. 8 is an exploded perspective view illustrating the configuration of the sensor section of the measuring apparatus shown in FIG. 6. FIG. 9 is an exploded perspective view illustrating the configuration of another example of the sensor section according to Embodiment 3 of the present invention.

As shown in FIG. 6, the measuring apparatus 40 according to Embodiment 3, in the same manner as the measuring apparatus 10 shown in FIG. 1 and FIG. 2 in Embodiment 1, has a sensor section 41, which operates as a sensor unit, a control unit 51, and a receiver 3. However, in contradistinction to Embodiment 1, in Embodiment 3, the sensor section 41 and computing section 22, which is included in a control unit 51, communicate not through wiring, but via wireless communication. The description below will concentrate on the differences between Embodiment 3 and Embodiment 1.

As shown in FIG. 6 and FIG. 7, unlike the sensor section 1 shown in FIG. 1 and FIG. 2 in Embodiment 1, in Embodiment 3, the sensor section 41 includes a signal transmitting unit 42. The signal transmitting unit 42 includes a signal processing section 43 and a transmitting section 44.

The signal processing section 43 detects the electric current flowing through the electrode 16a and electrode 16b (see FIG. 4) of the sensor 15, performs analog-to-digital conversion, and generates a digital signal that identifies the sensed current level. The transmitting section 44 wirelessly transmits the generated digital signal to the control unit 51 on a carrier wave.

In addition, as shown in FIG. 6 and FIG. 7, unlike the control unit 2 shown in FIG. 1 and FIG. 2 in Embodiment 1, the control unit 51 includes a receiving section 52. The receiving section 52 receives the signal transmitted from the signal transmitting unit 42 of the sensor section 41 and supplies it to the computing section 22. It should be noted that a digital signal has already been generated in the sensor section 41 from the electric current flowing though the electrode 16a and electrode 16b and the computing section 22 does not perform such processing in Embodiment 3. The computing section 22 stores the information identified from the digital signal in the memory section 23 and provides transmission-related instructions etc. to the transmitting section 24.

Then, in Embodiment 3, in the same manner as in Embodiment 1, the information stored in the memory section 23 is transmitted by the transmitting section 24 of the control unit 51 to the receiver 3 and the results of the measurements performed by the sensor 15 are subsequently displayed on the display screen of the display section 34 of the receiver 3. In Embodiment 3, in the same manner as in Embodiment 1, measurements are performed with the sensor section 41 disposed in a location removed from the control unit 51.

Therefore, when Embodiment 3 is used, the occurrence of situations where the sensor 15 is dislodged under the action of external forces is also minimized. Furthermore, the replacement of the sensor 15 is made even easier because the sensor section 41 and control unit 51 are connected wirelessly. In addition, even if the control unit 51 is dislodged under the action of external forces, the sensor 15 is not subsequently dislodged as a result.

In addition, as shown in FIG. 8, in Embodiment 3, the specific structure of the sensor section 41 can be a structure similar to the structure described with reference to FIG. 3 in Embodiment 1. In the example of FIG. 8, in addition to the sensor 15 and signal transmitting unit 42, the sensor section 41 includes a protective film 11, a support film 12, an adhesive film 13, and a water impermeable film 14. In the same manner as the base portion 15b of the sensor 15, the signal transmitting unit 42 is mounted on the support film 12 and is covered by the protective film 11. The support film 12 is affixed to the skin by the adhesive film 13 disposed on its bottom side.

Furthermore, as shown in FIG. 9, the specific structure of the sensor section 41 used in Embodiment 3 can be a structure similar to the structure described with reference to FIG. 5 in Embodiment 2. In the example of FIG. 9, in addition to the sensor 15 and signal transmitting unit 42, the sensor section 41 includes a protective film 11, a support film 17, two pieces of adhesive film 18, and a water impermeable film 19. In the same manner as the base portion 15b of the sensor 15, the signal transmitting unit 42 is mounted on the support film 17 and is covered by the protective film 11. However, in contradistinction to the example of FIG. 8, the support film 17 is affixed to the skin using two pieces of the adhesive film 18 on the upper face side.

It should be noted that in Embodiment 3 as well as in Embodiment 1, a sensor assembly is composed of the sensor section 41 and control unit 51. In addition, in the same manner as in Embodiment 1, the measuring apparatus 40 operates as a monitoring apparatus.

In addition, the measurement method according to Embodiment 3 includes the following Steps (A1)-(A9).

(A1) Disposing a sensor unit (sensor section 41), which includes a sensor 15, on the skin 4 such that the deployed portion 15a of the sensor is deployed under the skin.

(A2) Disposing a control unit 51 in a location removed from the sensor unit.

(A3) Affixing the sensor unit to the skin 4 using an adhesive film.

(A4) Covering the base portion 15b with a water impermeable film having an adhesive layer on one side, with the adhesive layer facing the base portion 15b of the sensor 15, and thereby preventing the penetration of moisture into the base portion 15b.

(A5) Directing the sensor 15 to output the signal.

(A6) Performing digital processing on the signal from the sensor 15 using the signal transmitting unit 42 and then wirelessly transmitting the generated digital signal to the control unit 51. It should be noted that amplification of the signal outputted by the sensor 15 is performed at such time if the signal transmitting unit 42 has an amplifier circuit.

(A7) Directing the computing section 22 to perform computational processing.

(A8) Wirelessly transmitting the outcome of the computational processing to an external location.

(A9) Receiving the transmitted outcome of computational processing using the receiver 3 and displaying numeric information about the substance based on the outcome of the computational processing.

Among these, the steps (A1), (A2), (A3), (A4), (A5), (A8), and (A9) respectively correspond to the steps (1), (3), (4), (5), (6), (9), and (10) of the measurement method according to Embodiment 1. On the other hand, while Steps (A6) and (A7) are not performed in Embodiment 1, they are performed in Embodiment 3. In addition, in Embodiment 3, Step (2) of the measurement method according to Embodiment 1 is not performed.

In addition, in the foregoing, the order of performance of the steps is not limited to the numbers assigned to the steps. For example, the steps may be performed in the following order: (A1) (A3), (A4), (A2), (A5), (A6), (A7), (A8), and (A9).

Embodiment 4

The measuring apparatus, control unit, sensor, sensor unit, monitoring apparatus, sensor assembly, and measurement method according to Embodiment 4 of the present invention will be hereinafter described with reference to FIG. 10-FIG. 13.

Figure 10:
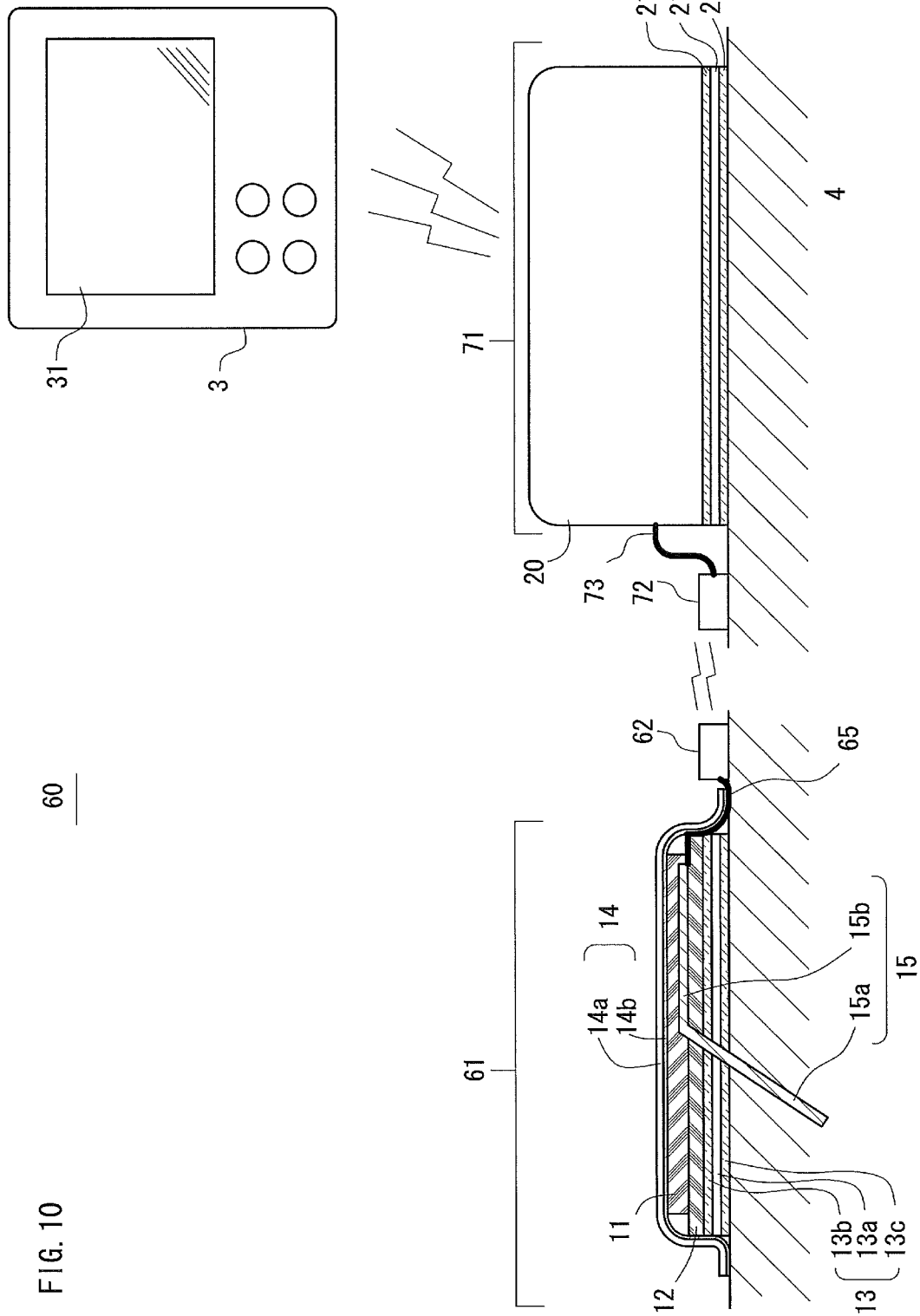
FIG. 10 is a block diagram illustrating the configuration of the measuring apparatus according to Embodiment 4 of the present invention, which is shown partially in cross-section.
Figure 11:
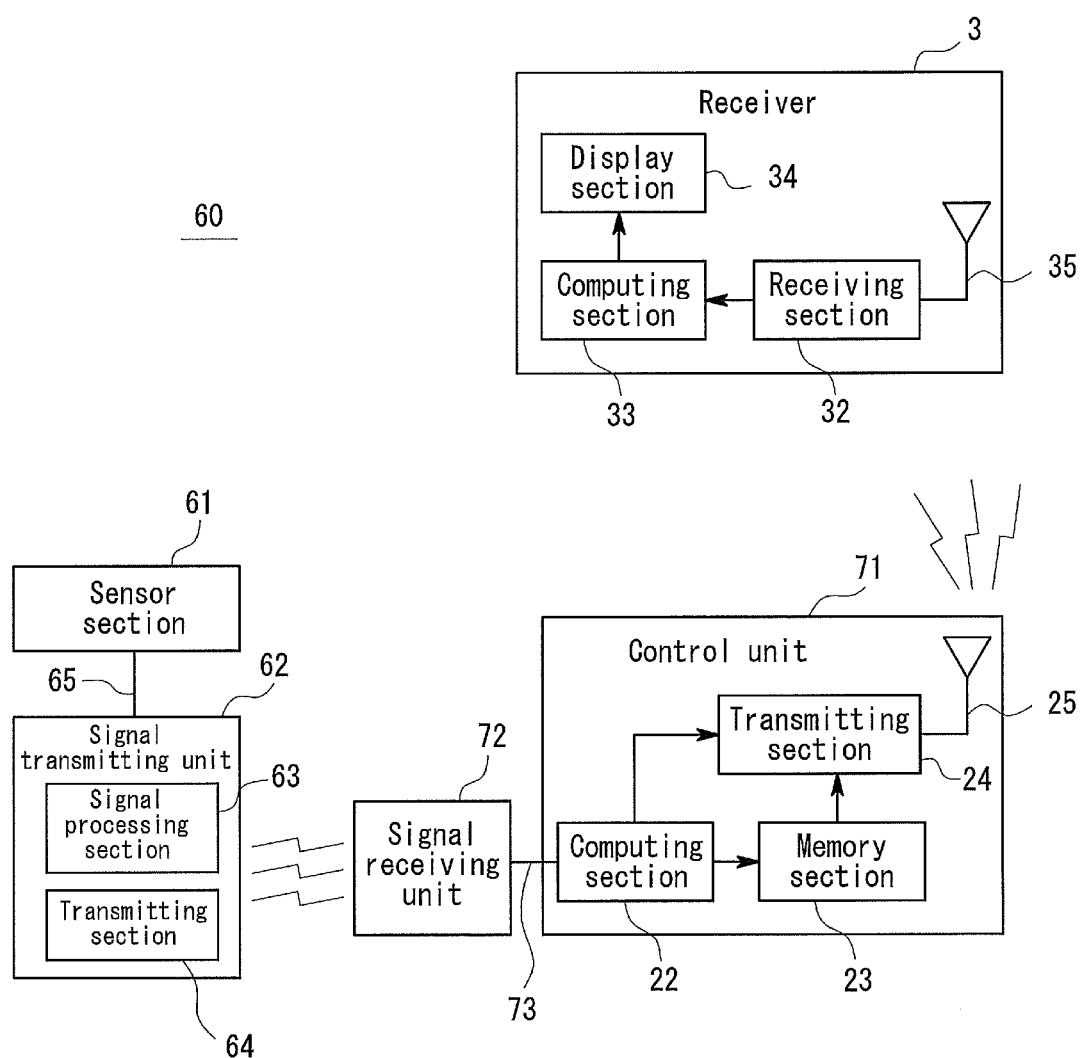
FIG. 11 is a block diagram illustrating the configuration of the measuring apparatus according to Embodiment 4 of the present invention.
Figure 12:
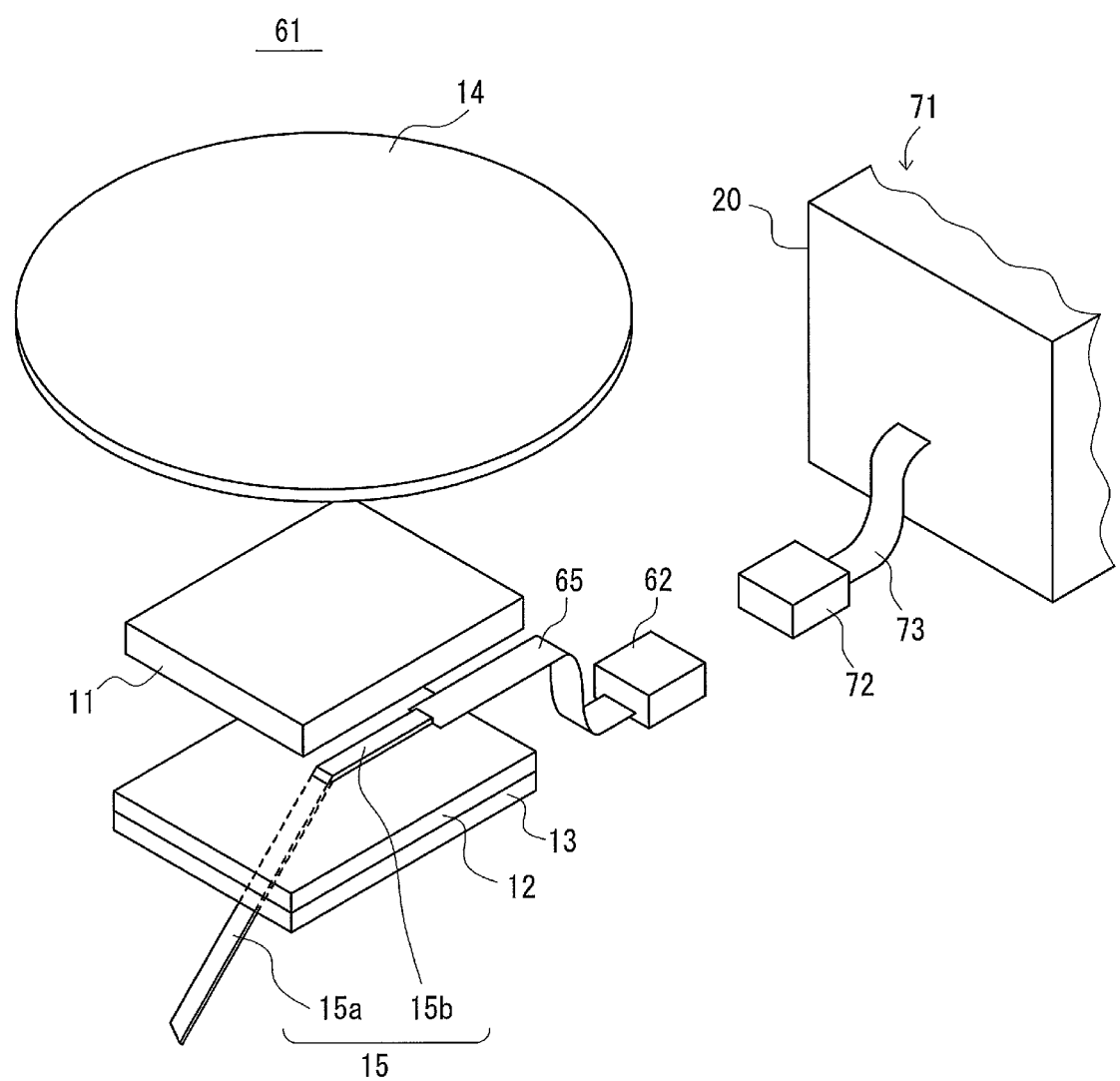
FIG. 12 is an exploded perspective view illustrating the configuration of the sensor section of the measuring apparatus shown in FIG. 10.
Figure 13:
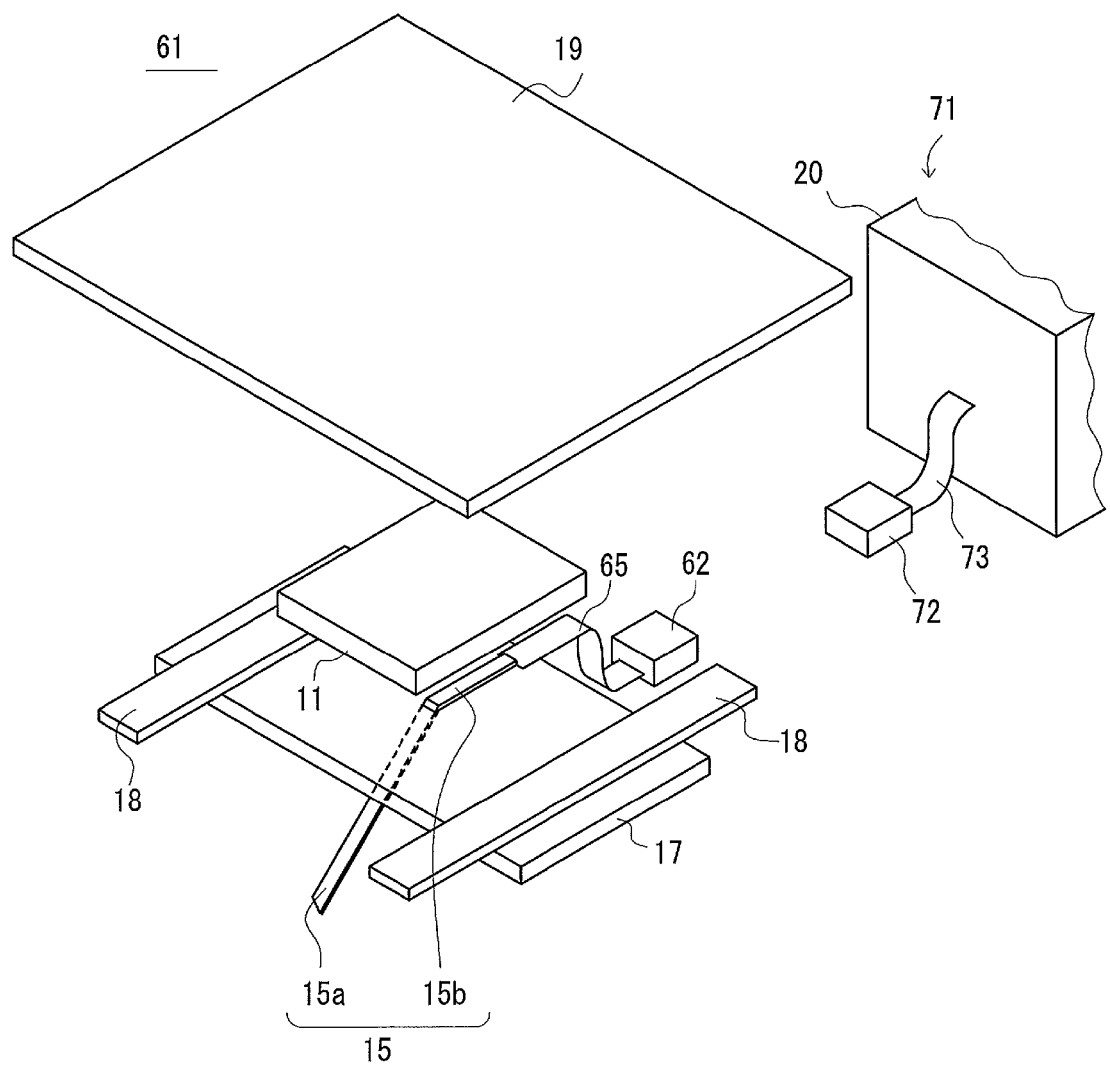
FIG. 13 is an exploded perspective view illustrating the configuration of another example of the sensor section according to Embodiment 4 of the present invention.

FIG. 10 is a diagram illustrating the configuration of the measuring apparatus according to Embodiment 4 of the present invention. In FIG. 10, the measuring apparatus is shown partially in cross-section. FIG. 11 is a block diagram illustrating the configuration of the measuring apparatus according to Embodiment 4 of the present invention. FIG. 12 is an exploded perspective view illustrating the configuration of the sensor section of the measuring apparatus shown in FIG. 10. FIG. 13 is an exploded perspective view illustrating the configuration of another example of the sensor section according to Embodiment 4 of the present invention.

As shown in FIG. 10, the measuring apparatus 60 according to Embodiment 4, in the same manner as the measuring apparatus 10 shown in FIG. 1 and FIG. 2 in Embodiment 1, has a sensor section 61, which operates as a sensor unit, a control unit 71, and a receiver 3. However, in contradistinction to Embodiment 1, in Embodiment 4, the sensor section 61 and computing section 22, which constitutes a control unit 71, communicate not through wiring, but via wireless communication. The description below will concentrate on the differences between Embodiment 4 and Embodiment 1.

As shown in FIG. 10 and FIG. 11, unlike the sensor section 1 shown in FIG. 1 and FIG. 2 in Embodiment 1, in Embodiment 4, the sensor section 61 is connected to a signal transmitting unit 62. The signal transmitting unit 62 is connected to the sensor 15 through a wire 65 and includes a signal processing section 63 and a transmitting section 64. It should be noted that the configuration shown in FIG. 10 and FIG. 11 is an illustration and, for instance, the signal transmitting unit 62 may only have the transmitting section 64 and the sensor section 61 may have the signal processing section 63.

Among these, the signal processing section 63 detects the electric current flowing through the electrode 16a and electrode 16b (see FIG. 4) of the sensor 15, performs analog-to-digital conversion, and generates a digital signal that identifies the sensed current level. The transmitting section 64 wirelessly transmits the generated digital signal to the control unit 71 on a carrier wave.

In addition, as shown in FIG. 10 and FIG. 11, unlike the control unit 2 shown in FIG. 1 and FIG. 2 in Embodiment 1, the control unit 71 is connected to a signal receiving unit 72. The signal receiving unit 72 receives the signal wirelessly transmitted from the signal transmitting unit 62 of the sensor section 61 and supplies it to the computing section 22.

In other words, in Embodiment 4, the sensor section 61 is configured in the same manner as the sensor section 41 shown in FIG. 6 and FIG. 7 in Embodiment 3, except that the signal transmitting unit 62 is not integrated with the sensor section 61. In addition, in Embodiment 4, the control unit 71 is configured in the same manner as the control unit 51 shown in FIG. 6 and FIG. 7 in Embodiment 3, except that the signal receiving unit 72 is not disposed in the housing 20 (see FIG. 6).

Furthermore, in Embodiment 4 as well as in Embodiment 3, a digital signal has already been generated in the sensor section 61 from the electric current flowing though the electrode 16a and electrode 16b and the computing section 22 does not perform such processing. In Embodiment 4, the computing section 22 stores the information identified from the digital signal in the memory section 23 and provides transmission-related instructions etc. to the transmitting section 24.

Based on such a configuration, in Embodiment 4 as well as in Embodiment 1, the information stored in the memory section 23 is transmitted by the transmitting section 24 of the control unit 71 to the receiver 3 and the results of the measurements performed by the sensor 15 are subsequently displayed on the display screen of the display section 34 of the receiver 3. In Embodiment 4, in the same manner as in Embodiment 1, measurements are performed with the sensor section 71 disposed in a location removed from the control unit 61.

Therefore, when Embodiment 4 is employed, the occurrence of situations in which the sensor 15 is dislodged under the action of external forces is also minimized. Furthermore, since the sensor section 61 and control unit 71 are connected wirelessly, the replacement of the sensor 15 is facilitated even more. In addition, even if the control unit 71 becomes detached under the action of external forces, the sensor 15 does not become dislodged following that.

In addition, in Embodiment 4, a reduction in the noise contained in the transmit signal is achieved because, in contradistinction to Embodiment 3, the signal transmitting unit 62 is not covered by a protective film and a water impermeable film. Furthermore, in Embodiment 4, an improvement in sensitivity to signals from the sensor section 61 is achieved because, in contradistinction to Embodiment 3, the signal receiving unit 72 is disposed outside the housing 20. In addition, an optimization of the location of the signal receiving unit 72 is accomplished as well.

In addition, as shown in FIG. 12, in Embodiment 4, the specific structure of the sensor section 61 can be a structure similar to the structure described with reference to FIG. 3 in Embodiment 1. In the example of FIG. 12, the sensor section 61 is configured in the same manner as the sensor section 1 shown in FIG. 3, except that the sensor 15 is connected to the signal transmitting unit 62 by the wire 65. In the same manner as the sensor section 1, in addition to the sensor 15, the sensor section 61 includes a protective film 11, a support film 12, an adhesive film 13, and a water impermeable film 14.

Furthermore, as shown in FIG. 13, the specific structure of the sensor section 61 used in Embodiment 4 can be a structure similar to the structure described with reference to FIG. 5 in Embodiment 2. In the example of FIG. 13, the sensor section 61 is configured in the same manner as the sensor section 7 shown in FIG. 5, except that the sensor 15 is connected to the signal transmitting unit 62 by the wire 65. In the same manner as the sensor section 7, in addition to the sensor 15, the sensor section 61 includes a protective film 11, a support film 17, two pieces of adhesive film 18, and a water impermeable film 19.

It should be noted that in the examples of FIG. 12 and FIG. 13, the signal receiving unit 72 is connected to the control unit 71 through the wire 73. In addition, in Embodiment 4 as well as in Embodiment 1, a sensor assembly is composed of the sensor section 61 and control unit 71. In addition, in the same manner as in Embodiment 1, the measuring apparatus 60 operates as a monitoring apparatus.

In addition, in Embodiment 4, a control unit whose signal receiving unit 72 is stored inside the housing 20, i.e. the control unit 51 shown in FIGS. 6-9 in Embodiment 3, may be used as the control unit. Furthermore, conversely, in Embodiment 3, a control unit whose signal receiving unit 72 is stored outside the housing 20, i.e. the control unit 71 shown in FIGS. 10-13 in Embodiment 4, may be used as the control unit.

In addition, the measurement method according to Embodiment 4 includes the following Steps (B1)-(B11).

(B1) Disposing a sensor unit (sensor section 61), which includes a sensor 15, on the skin 4 such that the deployed portion 15*a* of the sensor is deployed under the skin.

(B2) Disposing a signal transmitting unit 62 on the skin 4.

(B3) Disposing a control unit 71 in a location removed from the sensor unit.

(B4) Disposing a signal receiving unit 72 on the skin 4.

(B5) Affixing the sensor unit to the skin 4 using an adhesive film.

(B6) Covering the base portion 15*b* with a water impermeable film having an adhesive layer on one side, with the adhesive layer facing the base portion 15*b* of the sensor 15, and thereby preventing the penetration of moisture into the base portion 15*b*.

(B7) Directing the sensor 15 to output the signal.

(B8) Performing digital processing on the signal from the sensor 15 using the signal transmitting unit 62 and wirelessly transmitting the generated digital signal to the signal receiving unit 72 of the control unit 71. It should be noted that amplification of the signal outputted by the sensor 15 is performed at such time if the signal transmitting unit 62 has an amplifier circuit.

(B9) Directing the computing section 22 to perform computational processing.

(B10) Wirelessly transmitting the outcome of the computational processing to an external location.

(B11) Receiving the transmitted outcome of computational processing using the receiver 3 and displaying numeric information about the substance based on the outcome of the computational processing.

Among these, the steps (B1), (B3), (B5), (B6), (B7), (B9), (B10), and (B11) respectively correspond to the steps (1), (3), (4), (5), (6), (8), (9), and (10) of the measurement method according to Embodiment 1. On the other hand, while steps (B2), (B4), and (B8) are not performed in Embodiment 1, they are performed in Embodiment 4. In addition, in Embodiment 4, Step (2) of the measurement method according to Embodiment 1 is not performed.

In addition, in the foregoing, the order of performance of the steps is not limited to the numbers assigned to the steps. For example, the steps can be performed in the following order: (B1) (B5), (B6), (B2), (B3), (B4), (B7), (B8), (B9), (B10), and (B11).

(Modes of Use of the Measuring Apparatus)

The modes of use of the measuring apparatus shown in Embodiments 1-4 will be hereinafter described with reference to FIGS. 14-17. Although in the above-described Embodiments 1-4, the control unit is attached to the user's skin with a double-sided tape etc. (see FIG. 1, FIG. 6, and FIG. 10), in Modes of Use 1-3 illustrated below the control unit, which includes a computing section, is disposed on the user's garment.

[Mode of Use 1]

Figure 14:
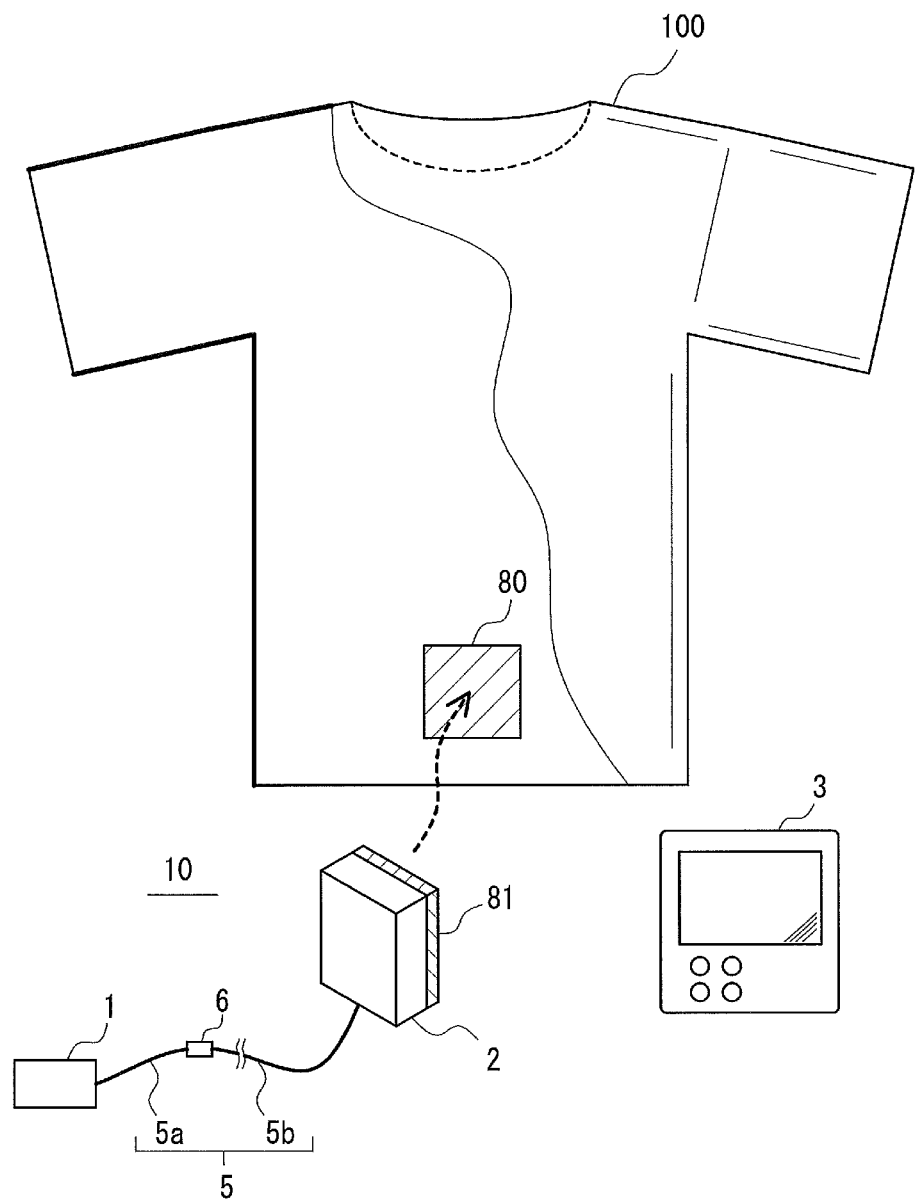
FIG. 14 is a diagram illustrating an exemplary mode of use (Mode of Use 1) of the measuring apparatus employed in the embodiments.

FIG. 14 is a diagram illustrating an exemplary mode of use (Mode of Use 1) of the measuring apparatus employed in the embodiments. The measuring apparatus 10 shown in FIG. 1 in Embodiment 1 is used in the example of FIG. 14. However, in Mode of Use 1, there are no limitations on the measuring apparatus and any measuring apparatuses described in any of Embodiments 2 to 4 may be used.

As shown in FIG. 14, in Mode of Use 1, the control unit 2, which contains a computing section (see FIG. 2), is disposed on the garment 100 of the user utilizing the measuring apparatus 10. In the example of FIG. 14, the control unit 2 is affixed to the garment 100 using a hook-and-loop fastener 81 attached thereto and a hook-and-loop fastener 80 attached to the garment 100.

In addition, in FIG. 14, the image on the left-hand side of the section line shows the items inside the garment 100. Since the hook-and-loop fastener 80 is provided inside the garment, the control unit 2 is also attached inside the garment 100. In Mode of Use 1, the control unit 2 is disposed such that it appears inconspicuous from the outside.

In addition, the structure used to attach the control unit 2 to the garment 100 can be any structure as long as it permits attachment and detachment according to the intent of the user, which may be a structure other than the hook-and-loop fasteners 80 and 81. Furthermore, the control unit 2 may be attached to the external surface of the garment. In such a case, the wire 5 connects the sensor section 1 with the control unit 2 through the hem of the garment 100 or a hole (not shown) provided in the garment 100.

In addition, unlike the control unit 2, the sensor section 1 is affixed to the skin of the user. In such a case, the method for affixing is not particularly limited and, in the same manner as in the example of FIG. 1, the sensor section 1 may be affixed using an adhesive film 13 (see FIG. 1) and the like. In addition, the sensor section 1 may be affixed using the configuration shown in FIG. 3 or using the configuration shown in FIG. 5.

If Mode of Use 1 described above is used, the control unit 2 is attached to the garment 100, as a result of which the occurrence of situations where the control unit 2 becomes dislodged from the user under the action of external forces due to the movements of the user is minimized. In addition, as a result, the occurrence of situations, in which the sensor unit 1, pulled by the control unit 2, becomes dislodged from the user, is minimized as well. In addition, when the user wishes to remove the control unit 2, it is sufficient to take off the garment 100 or simply detach it from the garment.

Furthermore, when the control unit 2 is separated from the sensor section 1 by removing the connector 6 that connects the two and the user puts on a garment 100 having a new control unit 2 attached thereto and then re-connects them, measurements are performed by the existing sensor section 1 and the new control unit 2. The receiver 3 then receives the outcome of the computational processing from the new control unit 2.

In addition, as a result, in accordance with Mode of Use 1, the user can replace the sensor section 1 and control unit 2 in a respectively independent and simple manner. In other words, when replacing one of the items above, the user can accomplish the replacement without paying attention to the other item.

[Mode of Use 2]

Figure 15:
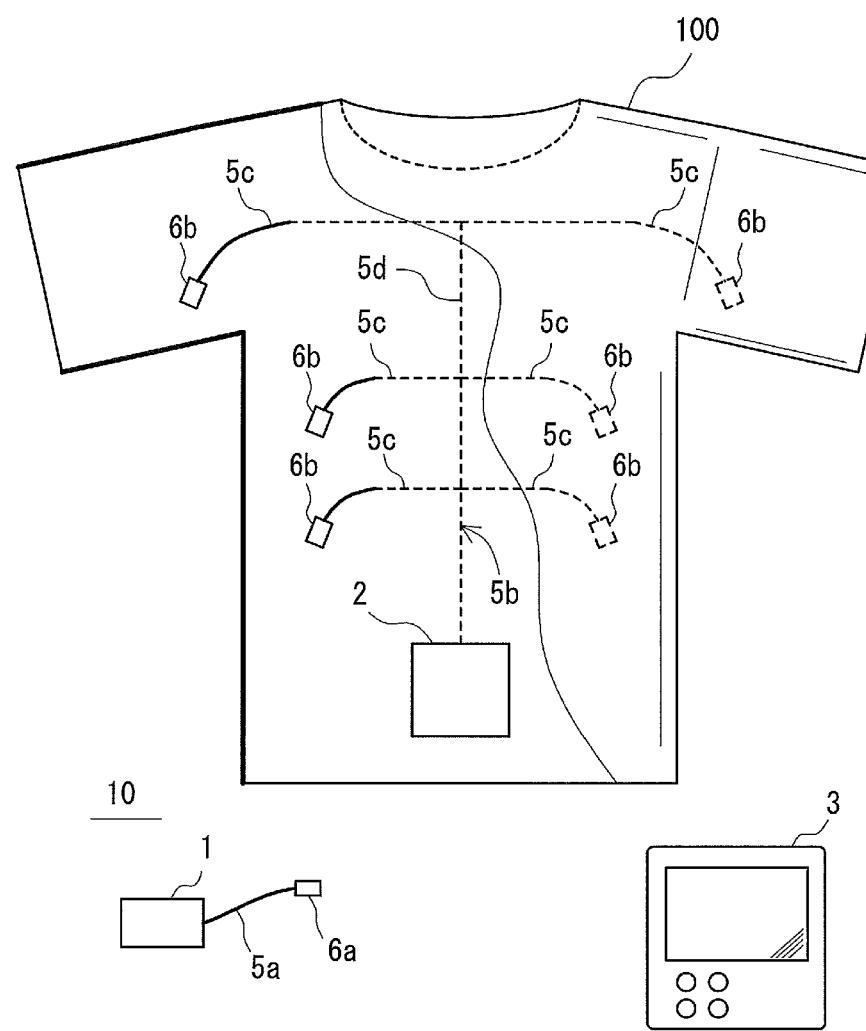
FIG. 15 is a diagram illustrating an exemplary mode of use (Mode of Use 2) of the measuring apparatus employed in the embodiments.

FIG. 15 is a diagram illustrating an exemplary mode of use (Mode of Use 2) of the measuring apparatus employed in the embodiments. The measuring apparatus 10 shown in FIG. 1 in Embodiment 1 is used in Mode of Use 2 shown in FIG. 15. It should be noted that the measuring apparatus shown in FIG. 5 in Embodiment 2 can be also utilized in Mode of Use 2.

As shown in FIG. 15, also in Mode of Use 2, the control unit 2 is disposed on the user's garment 100. The example of FIG. 15 illustrates a state, in which the control unit 2 is attached to the garment. In addition, in the example of FIG. 15, the attachment of the control unit 2 to the garment is accomplished using the structures discussed in Mode of Use 1 such as, for example, hook-and-loop fasteners, as a result of which the control unit 2 is attached to the garment 100.

However, in Mode of Use 2, the control unit 2 may be affixed such that it is not easily dislodged from the garment 100. For example, the control unit 2 may be affixed using an adhesive tape and the like and, alternatively, a certain portion of the garment 100 may be having two fabric layers and the unit inserted between the layers of the fabric. Furthermore, in Mode of Use 2, the control unit 2 may be made up of multiple units, in which case each unit is affixed to the garment 100 on an individual basis.

In addition, as shown in FIG. 15, in Mode of Use 2, the wire 5b of the control unit 2 is composed of the wire 5d and multiple wires 5c branching off of it. In addition, a female terminal 6b, which can be connected to a male terminal 6a in the sensor section 1 (see FIG. 3), is provided at the distal end of each wire 5c. Furthermore, a portion of the wires 5c and the female terminals 6b at the distal ends thereof are detached from the garment, while the remaining portion of the wires 5c and the wires 5d are affixed to the garment 100. In FIG. 15, a portion of the wires 5c and the female terminals 6b protrude from the garment 100.

It should be noted that the wires affixed to the garment 100 on the left-hand side of the section line in FIG. 15 are shown as short dash lines. In addition, sewing the wires to the fabric or using an adhesive tape is suggested as a method for affixing the wires to the garment 100. In addition, a fastening method is proposed, in which the portion where the wires are disposed has two layers and the wires are inserted between the layers of fabric.

In addition, the sensor section 1 is affixed to the skin of the user in the same manner as in Mode of Use 1, but the sensor section 1 is connected to the control unit 2 through the wire 5c and female terminal 6b positioned closest thereto. Therefore, Mode of Use 2 allows for the degree of freedom of the mounting position of the sensor section 1 to be raised and achieves a reduction in the burden on the user. Further, all the effects described in Mode of Use 1 can be obtained when Mode of Use 2 is used.

[Mode of Use 3]

Figure 16:
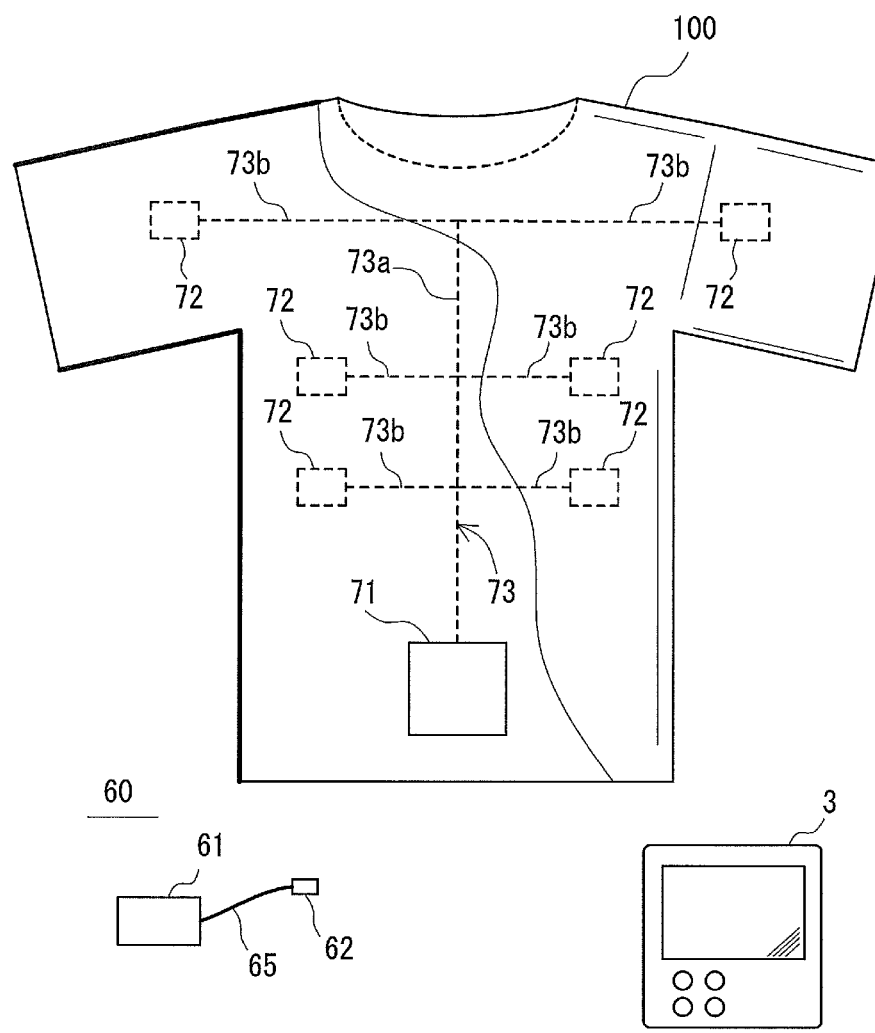
FIG. 16 is a diagram illustrating an exemplary mode of use (Mode of Use 3) of the measuring apparatus employed in the embodiments.

FIG. 16 is a diagram illustrating an exemplary mode of used (Mode of Use 3) of the measuring apparatus employed in the embodiments. The measuring apparatus 60 shown in FIG. 10 in Embodiment 4 is used in Mode of Use 3 shown in FIG. 16.

As shown in FIG. 16, in Mode of Use 3, the control unit 71 is disposed on the user's garment 100. The example of FIG. 16 illustrates a state, in which the control unit 71 is attached to the garment. In addition, in the example of FIG. 16, the attachment of the control unit 71 to the garment is accomplished using the structures discussed in Mode of Use 1 such as, for example, hook-and-loop fasteners, as a result of which the control unit 71 is attached to the garment 100.

However, in Mode of Use 3, in the same manner as in Mode of Use 2, the control unit 71 may be affixed such that it is not easily dislodged from the garment 100. For example, the control unit 71 may be affixed using an adhesive tape and the like and, alternatively, a certain portion of the garment 100 may be having two fabric layers and the unit inserted between the layers of the fabric. Furthermore, in Mode of Use 3, in the same manner as in Mode of Use 2, the control unit 71 may be made up of multiple units, in which case each unit is affixed to the garment 100 on an individual basis.

In addition, as shown in FIG. 16, in Mode of Use 3, the wire 73 of the control unit 71 is composed of the wire 73a and multiple wires 73b branching off of it. In addition, a signal receiving unit 72 is connected to the distal end of each wire 73b. Furthermore, the wire 73a, wires 73b, and signal receiving units 72 are affixed to the garment 100.

Sewing the wires to the fabric or using an adhesive tape is suggested as a method for affixing the wire 73a, wires 73b, and the signal receiving unit 72 to the garment 100. In addition, a fastening method is proposed, in which the portion where the wires or the signal receiving unit 72 are disposed has two fabric layers and the wires or the signal receiving unit 72 are inserted between the layers of fabric.

In addition, the sensor section 61 and signal transmitting unit 62 are affixed to the skin of the user and, at such time, the signal receiving unit 72 located closest to the signal transmitting unit 62 receives the signal from the signal transmitting unit 62. Therefore, Mode of Use 3 allows the control unit 71 to receive the signal from of the sensor section 61 using the signal receiving unit 72 that receives the strongest signal. Mode of Use 3 allows for the degree of freedom of the mounting position of the sensor section 61 to be raised while minimizing the generation of signal reception errors.

Further, all the effects described in Mode of Use 1 can be obtained when Mode of Use 3 is utilized. Furthermore, in Mode of Use 3, the sensor section 41 shown in FIG. 6 in Embodiment 3 can be used instead of the sensor section 61. In this case, the above-described effects can also be obtained.

[Mode of Use 4]

Figure 17:
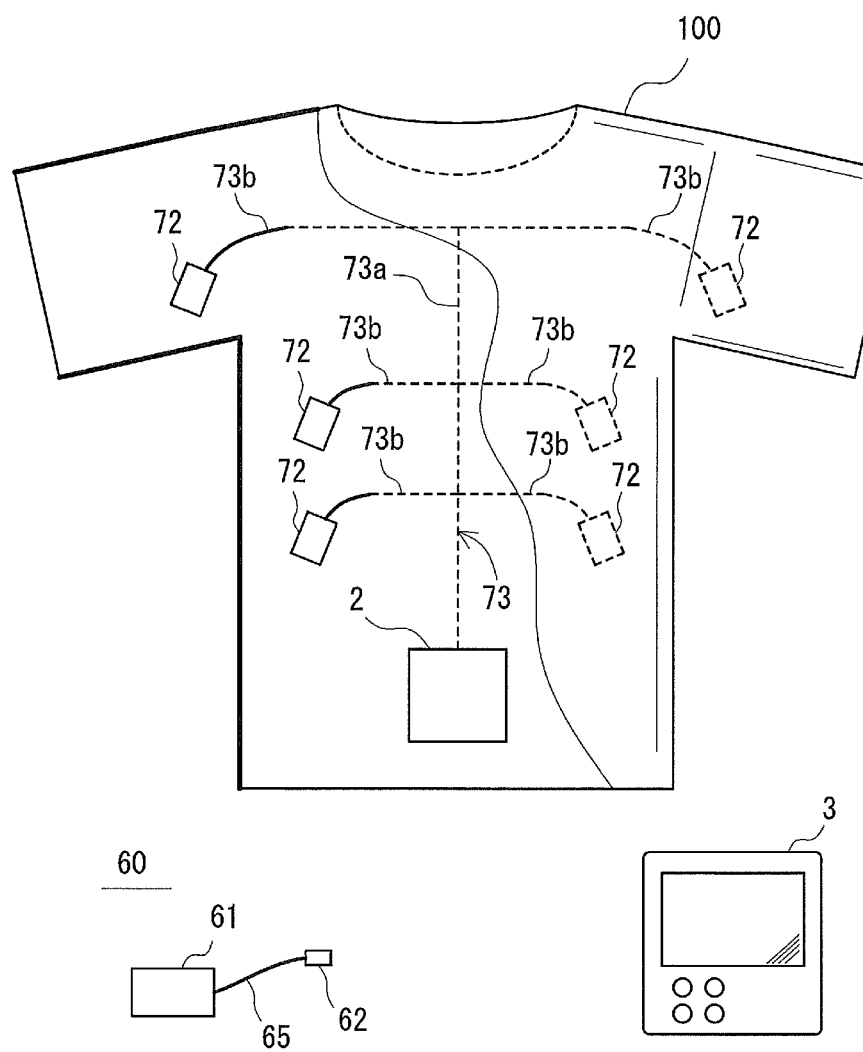
FIG. 17 is a diagram illustrating an exemplary mode of use (Mode of Use 4) of the measuring apparatus employed in the embodiments.
Figure 18:
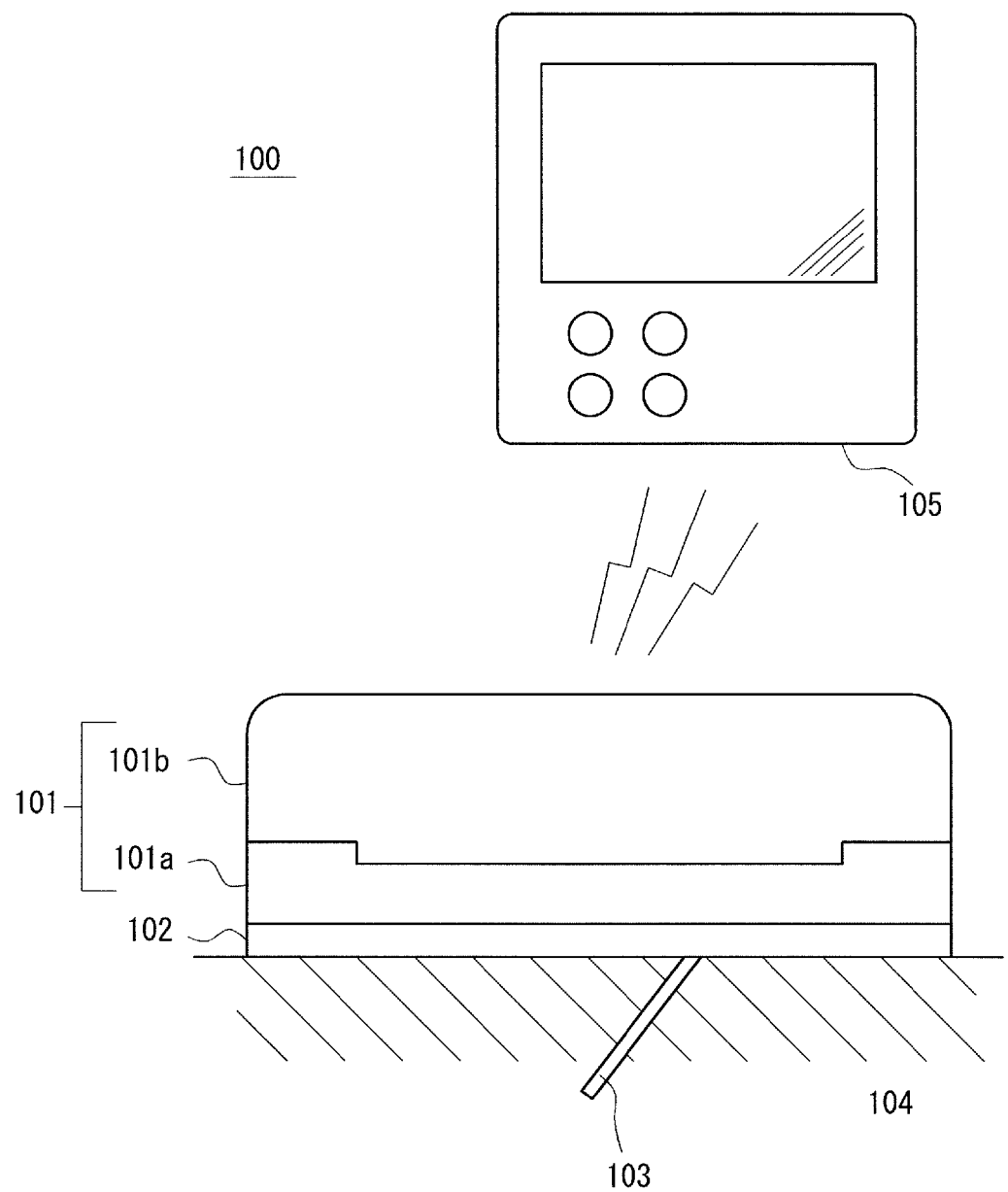
FIG. 18 shows an example of a traditional measuring apparatus.

FIG. 17 is a diagram illustrating an exemplary mode of use (Mode of Use 4) of the measuring apparatus employed in the embodiments. The measuring apparatus 60 shown in FIG. 10 in Embodiment 4 is used in Mode of Use 4 shown in FIG. 17 in the same manner as in Mode of Use 3. Mode of Use 4 differs from Mode of Use 3 in the configuration of the wire 73. The discussion below will concentrate on its differences from Mode of Use 3.

As shown in FIG. 17, in Mode of Use 4, in the same manner as in Mode of Use 3, the wire 73 is composed of the wire 73*a* and multiple wires 73*b* branching off of it, with a signal receiving unit 72 connected to the distal end of each wire 73*b*.

However, in Mode of Use 4, in contradistinction to Mode of Use 3, a portion of the wires 73*b* and signal receiving units 72, are not affixed to the garment 100 and stand out from the garment. In FIG. 17, a portion of the wires 73*b* and the signal receiving units 72 stand out from the garment 100. On the one hand, the remaining portion of the wires 73*b* and wire 73*a* are affixed to the garment.

In other words, the wire 73 is disposed in the same manner as the wire 5*b* in Mode of Use 2, which is illustrated in FIG. 15. It should be noted that the fastening described in Mode of Use 2 is suggested as the method for affixing the wire. In addition, the wires affixed to the garment 100 on the left-hand side of the section line in FIG. 17 are shown as short dash lines.

Thus, if Mode of Use 4 is employed, a higher degree of freedom can be imparted to the location of the signal receiving unit 72 and, in comparison with Mode of Use 3, the signal receiving unit 72 can be brought closer to the signal transmitting unit 61. Accordingly, the generation of signal reception errors can be suppressed even more.

Further, all the effects described in Mode of Use 1 can be obtained when Mode of Use 4 is utilized. Furthermore, in Mode of Use 4, the sensor section 41 shown in FIG. 6 in Embodiment 3 can be used instead of the sensor section 61. In this case, the above-described effects can also be obtained.

Although some or all of the above-described embodiments can be expressed in the form of the following (Supplementary note 1)-(Supplementary note 43), they are not limited thereto.

(Supplementary Note 1)

A control unit comprising a computing section that, when an external sensor outputs a signal in accordance with numeric information about a substance contained in at least one carrier selected from subcutaneous interstitial fluid and blood, receives the signal outputted by the sensor and performs computational processing based on the signal.

(Supplementary Note 2)

The control unit according to Supplementary Note 1, further comprising a wire that electrically connects the sensor to the computing section.

(Supplementary Note 3)

The control unit according to Supplementary Note 1, wherein the computing section receives signals outputted by the sensor via wireless communication.

(Supplementary Note 4)

The control unit according to any one of Supplementary Notes 1-3, further comprising a transmitting section wirelessly transmitting the outcome of the computational processing performed by the computing section to an external location and a housing containing both the computing section and the transmitting section.

(Supplementary Note 5)

A sensor for measuring numeric information about a substance contained in at least one carrier selected from subcutaneous interstitial fluid and blood, the sensor comprising a wire for external connections.

(Supplementary Note 6)

A sensor for measuring numeric information about a substance contained in at least one carrier selected from subcutaneous interstitial fluid and blood, the sensor comprising a signal transmitting unit that transmits the signal outputted by said sensor to an external location via wireless communication.

(Supplementary Note 7)

A sensor unit comprising a sensor for measuring numeric information about a substance contained in at least one carrier selected from subcutaneous interstitial fluid and blood.

(Supplementary Note 8)

The sensor unit according to Supplementary Note 7, further comprising a wire connected to the sensor.

(Supplementary Note 9)

The sensor unit according to Supplementary Note 7, further comprising a signal transmitting unit that transmits signals outputted by the sensor to an external location via wireless communication.

(Supplementary Note 10)

The sensor unit according to any one of Supplementary Notes 7-9, further comprising a water impermeable film having an adhesive layer on one side, wherein the sensor comprises a deployed portion deployed under the skin and a base portion disposed on the surface of the skin; and, the water impermeable film is formed so as to prevent the ingress of moisture to the base portion when it covers the base portion with the adhesive layer facing the base portion.

(Supplementary Note 11)

The sensor unit according to Supplementary Note 10, further comprising an adhesive film for affixing said sensor unit to the skin.

(Supplementary Note 12)

The sensor unit according to Supplementary Note 11, comprising, as the adhesive film, two or more pieces of adhesive film having an adhesive layer on one side, and wherein the two or more pieces of adhesive film are strip-like in shape and are capable of adhesion to both said sensor unit and to the skin through the medium of the adhesive layer in respectively different locations on the upper face of said sensor unit.

(Supplementary Note 13)

A monitoring apparatus that monitors numeric information about a substance contained in at least one carrier selected from subcutaneous interstitial fluid and blood, comprising:

a sensor section having a sensor outputting a signal in accordance with the numeric information, and a computing section that receives the signal outputted by the sensor and performs computational processing based on the signal, the sensor being formed such that a portion thereof can be deployed under the skin, and the computing section being disposed so as to be isolated from the sensor section.

(Supplementary Note 14)

The monitoring apparatus according to Supplementary Note 13, wherein the computing section is electrically connected to the sensor section through a wire.

(Supplementary Note 15)

The monitoring apparatus according to Supplementary Note 13, wherein the computing section communicates with the sensor section via wireless communication.

(Supplementary Note 16)

The monitoring apparatus according to Supplementary Note 14, wherein a connecting structure that permits selection between a connected state and a disconnected state is provided in the wire.

(Supplementary Note 17)

The monitoring apparatus according to any one of Supplementary Notes 13-16, wherein the sensor section further comprises a water impermeable film having an adhesive layer on one side, and the sensor comprises a deployed portion deployed under the skin and a base portion disposed on the surface of the skin; and, the water impermeable film is formed so as to prevent the ingress of moisture to the base portion when it covers the base portion with the adhesive layer facing the base portion.

(Supplementary Note 18)

The monitoring apparatus according to Supplementary Note 17, wherein the sensor section further comprises an adhesive film for affixing said sensor section to the skin.

(Supplementary Note 19)

The monitoring apparatus according to Supplementary Note 18, wherein the sensor section comprises, as the adhesive film, two or more pieces of adhesive film having an adhesive layer on one side, and the two or more pieces of adhesive film are strip-like in shape and are capable of adhesion to both said sensor section and the skin through the medium of the adhesive layer in respectively different locations on the upper face of said sensor section.

(Supplementary Note 20)

The monitoring apparatus according to any one of Supplementary Notes 13-19, further comprising a transmitting section wirelessly transmitting the outcome of the computational processing performed by the computing section to an external location, and a housing containing both the computing section and the transmitting section.

(Supplementary Note 21)

The monitoring apparatus according to Supplementary Note 20, further comprising a receiver that receives the outcome of the computational processing transmitted by the transmitting section and displays numeric information about the substance based on the outcome of the computational processing.

(Supplementary Note 22)

The monitoring apparatus according to Supplementary Note 14, further comprising an amplifier circuit that amplifies signals outputted by the sensor, wherein the amplifier circuit is provided in at least one location selected from the sensor section and the wire.

(Supplementary Note 23)

A sensor assembly that measures numeric information about a substance contained in at least one carrier selected from subcutaneous interstitial fluid and blood, comprising:

a sensor section that has a sensor outputting a signal in accordance with the numeric information, and a computing section that receives the signal outputted by the sensor and performs computational processing based on the signal, the sensor being formed such that a portion thereof can be deployed under the skin, and the computing section being disposed so as to be isolated from the sensor section.

(Supplementary Note 24)

The sensor assembly according to Supplementary Note 23, wherein the computing section is electrically connected to the sensor section through a wire.

(Supplementary Note 25)

The sensor assembly according to Supplementary Note 23, wherein the computing section communicates with the sensor section via wireless communication.

(Supplementary Note 26)

The sensor assembly according to Supplementary Note 24, wherein a connecting structure that permits selection between a connected state and a disconnected state is provided in the wire.

(Supplementary Note 27)

The sensor assembly according to any one of Supplementary Notes 23-26, wherein the sensor section further comprises a water impermeable film having an adhesive layer on one side, and the sensor comprises a deployed portion deployed under the skin and a base portion disposed on the surface of the skin; and, the water impermeable film is formed so as to prevent the ingress of moisture to the base portion when it covers the base portion with the adhesive layer facing the base portion.

(Supplementary Note 28)

The sensor assembly according to Supplementary Note 27, wherein the sensor section further comprises an adhesive film for affixing said sensor section to the skin.

(Supplementary Note 29)

The sensor assembly according to Supplementary Note 28, wherein the sensor section comprises, as the above-mentioned adhesive film, two or more pieces of adhesive film having an adhesive layer on one side, and the two or more pieces of adhesive film are strip-like in shape and are capable of adhesion to both said sensor section and the skin through the medium of the adhesive layer in respectively different locations on the upper face of said sensor section.

(Supplementary Note 30)

The sensor assembly according to any one of Supplementary Notes 23-29, further comprising a transmitting section wirelessly transmitting the outcome of the computational processing performed by the computing section to an external location, and a housing containing both the computing section and the transmitting section.

(Supplementary Note 31)

The sensor assembly according to Supplementary Note 30, further comprising a receiver that receives the outcome of the computational processing transmitted by the transmitting section and displays numeric information about the substance based on the outcome of the computational processing.

(Supplementary Note 32)

The sensor assembly according to Supplementary Note 24, further comprising an amplifier circuit that amplifies the signals outputted by the sensor, wherein the amplifier circuit is provided in at least one location selected from the sensor section and the wire.

(Supplementary Note 33)

A measurement method for measuring numeric information about a substance contained in at least one carrier selected from subcutaneous interstitial fluid and blood, the method comprising the steps of:

(a) disposing a sensor unit having a sensor outputting a signal in accordance with the numeric information on the skin such that a portion of the sensor is deployed under the skin, and (b) disposing a control unit including a computing section that receives the signal outputted by the sensor and performs computational processing based on the signal, in a location removed from the sensor unit.

(Supplementary Note 34)

The measurement method according to Supplementary Note 33, further comprising the step of (c) electrically connecting the control unit to the sensor unit through a wire.

(Supplementary Note 35)

The measurement method according to Supplementary Note 33, further comprising the step of (d) allowing the control unit and the sensor unit to communicate via wireless communication.

(Supplementary Note 36)

The measurement method according to any one of Supplementary Notes 33-35, further comprising the steps of (e) causing the sensor to output the signal, and (f) causing the computing section to perform the computational processing.

(Supplementary Note 37)

The measurement method according to Supplementary Note 34, wherein in the step (c), a connecting structure that permits selection between a connected state and a disconnected state is provided in the wire.

(Supplementary Note 38)

The measurement method according to any one of Supplementary Notes 33-37, in a situation where the sensor comprises a deployed portion deployed under the skin and a base portion disposed on the surface of the skin, further comprising the step of (g) using a water impermeable film having an adhesive layer on one side, with the adhesive layer facing the base portion, to cover the base portion so as to prevent the ingress of moisture to the base portion.

(Supplementary Note 39)

The measurement method according to Supplementary Note 38, further comprising the step of (h) affixing the sensor unit to the skin using an adhesive film.

(Supplementary Note 40)

The measurement method according to Supplementary Note 39, wherein in the step (h), two or more pieces of adhesive film that have an adhesive layer on one side and are strip-like in shape are used as the adhesive film, and the two or more pieces of adhesive film are adhered to both said sensor unit and to the skin through the medium of the adhesive layer in respectively different locations on the upper face of said sensor unit.

(Supplementary Note 41)

The measurement method according to Supplementary Note 36, further comprising the step of (i) wirelessly transmitting the outcome of the computational processing to an external location after completion of the step (f).

(Supplementary Note 42)

The measurement method according to Supplementary Note 41, further comprising the step of (j) receiving the outcome of the computational processing transmitted in step (i) and displaying numeric information about the substance based on the outcome of the computational processing.

(Supplementary Note 43)

The measurement method according to any one of Supplementary Notes 33-42, further comprising the step of (k) amplifying the signal outputted by the sensor.

While the invention of the present application has been described above with reference to embodiments, the invention of the present application is not limited to the above-described embodiments. It will be appreciated by those of ordinary skill in the art that various changes in the form and details of the invention of the present application can be made within the scope of the invention of the present application.

This Application is based upon and claims the benefit of priority from Japanese Patent Application 2009-218794 filed on Sep. 24, 2009, the disclosure of which is incorporated herein in its entirety.

INDUSTRIAL APPLICABILITY

As described above, when measurements are performed by deploying a sensor in the body, the present invention can minimize the occurrence of situations in which the sensor becomes dislodged contrary to the intent of the user and, furthermore, can facilitate the operation of sensor replacement. For this reason, the present invention possesses industrial applicability and is suitable for use in measuring equipment for measuring numeric information concerning substances contained in at least one carrier selected from subcutaneous interstitial fluid and blood, in particular, information concerning glucose concentration.

DESCRIPTION OF THE REFERENCE NUMERALS

1 Sensor section
2 Control unit
3 Receiver
4 Skin
5 Wire
6 Connector
7 Sensor section
10 Measuring apparatus
11 Protective film
12 Support film
13 Adhesive film
13a Base material
13b, 13c Adhesive layers
14 Water impermeable film
14a Base material
14b Adhesive layer
15 Sensor
15a Deployed portion
15b Base portion
17 Support film
18 Adhesive film
19 Water impermeable film
20 Housing
21 Adhesive film for affixing the control unit
21a Base material
21b, 21c Adhesive layers
22 Computing section
23 Memory section
24 Transmitting section
25 Antenna
31 Display screen
32 Receiving section
33 Computing section
34 Display section
35 Antenna
40 Measuring apparatus
41 Sensor section 42 Signal transmitting unit
43 Signal processing section
44 Transmitting section
51 Control unit
52 Receiving section
60 Measuring apparatus
61 Sensor section
62 Signal transmitting unit
63 Signal processing section
64 Transmitting section
65 Wire
71 Control unit
72 Signal receiving unit
73 Wire
80, 81 Hook-and-loop fasteners
100 Garment

The invention claimed is:

1. A measuring apparatus that measures numeric information about a substance contained in at least one carrier selected from subcutaneous interstitial fluid and blood, comprising:
 a sensor section having a sensor outputting a signal in accordance with the numeric information, a support film that supports the sensor, and an adhesive film that affixes the sensor section to the skin; and
 a computing section that is disposed on a garment of a user utilizing said measuring apparatus and receives the signal outputted by the sensor and performs computational processing based on the signal,
 the sensor comprising a deployed portion deployed under the skin and a base portion disposed over the surface of the skin, and
 the computing section being disposed so as to be isolated from the sensor section, wherein
 when the deployed portion extends not through the adhesive film but through the support film and the base portion is disposed on the support film, the sensor is supported by the support film and the deployed portion is deployed under the skin,
 the sensor section comprises, as the adhesive film, two or more pieces of adhesive film having a first adhesive layer on one side, and
 the two or more pieces of adhesive film are strip-like in shape and are capable of adhesion to both said sensor section and the skin through the medium of the first adhesive layer of the adhesive film in respectively different locations on an upper face of said sensor section,
 wherein the computing section communicates with the sensor section via wireless communication,
 wherein the sensor section includes a water impermeable film having a second adhesive layer on one side, and the water impermeable film is formed so as to prevent the ingress of moisture to the base portion when it covers the base portion with the second adhesive layer facing the base portion, the second adhesive layer of the water impermeable film being configured to be in contact with the skin, and
 the sensor section includes a signal transmitting unit connected to the sensor through a wire, and the signal transmitting unit is not covered by the water impermeable film.

2. The measuring apparatus according to claim 1, further comprising a transmitting section wirelessly transmitting the outcome of the computational processing performed by the computing section to an external location, and
 a housing containing both the computing section and the transmitting section.

3. The measuring apparatus according to claim 2, further comprising a receiver that receives the outcome of the computational processing transmitted by the transmitting section and displays numeric information about the substance based on the outcome of the computational processing.

4. The measuring apparatus according to claim 1, further comprising an amplifier circuit that amplifies the signal outputted by the sensor,
 wherein the amplifier circuit is provided in at least one location selected from the sensor section and a portion electrically connected to the sensor section.

5. A measurement method for measuring numeric information about a substance contained in at least one carrier selected from subcutaneous interstitial fluid and blood, the method comprising the steps of:
 providing a sensor unit having a sensor outputting a signal in accordance with the numeric information, a support film that supports the sensor, and an adhesive film that affixes the sensor section to the skin,
 disposing the sensor unit on the skin such that a deployed portion of the sensor is deployed under the skin and a base portion of the sensor is disposed over the surface of the skin,
 disposing a control unit on a garment of a user utilizing said measuring apparatus, the control unit including a computing section that receives the signal outputted by the sensor and performs computational processing based on the signal, in a location removed from the sensor unit, wherein
 when the deployed portion extends not through the adhesive film but through the support film and the base portion is disposed on the support film, the sensor is supported by the support film and the deployed portion is deployed under the skin,
 the sensor section comprises, as the adhesive film, two or more pieces of adhesive film having a first adhesive layer on one side, and
 the two or more pieces of adhesive film are strip-like in shape and are capable of adhesion to both said sensor section and the skin through the medium of the first adhesive layer of the adhesive film in respectively different locations on an upper face of said sensor section,
 wherein the method further comprises the step of allowing the control unit and the sensor unit to communicate via wireless communication,
 disposing a water impermeable film having a second adhesive layer on one side, the water impermeable film being formed so as to prevent the ingress of moisture to the base portion when it covers the base portion with the second adhesive layer facing the base portion, and the second adhesive layer of the water impermeable film being configured to be in contact with the skin, and
 providing a signal transmitting unit connected to the sensor through a wire, the signal transmitting unit being not covered by the water impermeable film.

6. The measuring apparatus according to claim 1, wherein the support film is configured to be disposed between the base portion and the skin, and
 the adhesive film is configured to be disposed on the skin and a surface of the support film opposite to a surface facing the skin.

* * * * *